(12) United States Patent
Nyce et al.

(10) Patent No.: US 9,598,328 B2
(45) Date of Patent: Mar. 21, 2017

(54) INTEGRATED PROCESSES AND SYSTEMS FOR CONVERSION OF METHANE TO MULTIPLE HIGHER HYDROCARBON PRODUCTS

(71) Applicant: Siluria Technologies, Inc., San Francisco, CA (US)

(72) Inventors: Greg Nyce, Pleasanton, CA (US); Erik C. Scher, San Francisco, CA (US); Ajay Madgavkar, Katy, TX (US); Samuel Weinberger, San Francisco, CA (US); Rahul Iyer, Kensington, CA (US); Lawrence Peck, Glen Ellyn, IL (US); Joel Herger, Houston, TX (US); Benjamin Saydah, Oak Park, IL (US)

(73) Assignee: SILURIA TECHNOLOGIES, INC., San Francisco, CA (US)

( * ) Notice: Subject to any disclaimer, the term of this patent is extended or adjusted under 35 U.S.C. 154(b) by 323 days.

(21) Appl. No.: 14/099,614

(22) Filed: Dec. 6, 2013

(65) Prior Publication Data

US 2014/0171707 A1    Jun. 19, 2014

Related U.S. Application Data

(60) Provisional application No. 61/734,865, filed on Dec. 7, 2012.

(51) Int. Cl.
*C07C 2/04* (2006.01)
*C07C 2/84* (2006.01)
(Continued)

(52) U.S. Cl.
CPC ............. *C07C 2/04* (2013.01); *C07C 2/82* (2013.01); *C07C 2/84* (2013.01); *C10G 50/00* (2013.01);
(Continued)

(58) Field of Classification Search
CPC .. C07C 2/84; C07C 11/04; C07C 2/04; C07C 2/82; F25J 2205/04; F25J 2210/12;
(Continued)

(56) References Cited

U.S. PATENT DOCUMENTS 2,486,980 A    11/1949  Robinson
2,579,601 A    12/1951  Nelson et al.
(Continued)

FOREIGN PATENT DOCUMENTS

CA    2765769 A1    1/2011
CN    1403375 A    3/2003
(Continued)

OTHER PUBLICATIONS

U.S. Appl. No. 13/115,082, filed May 24, 2011, Scher et al.
(Continued)

*Primary Examiner* — Sharon Pregler
(74) *Attorney, Agent, or Firm* — Wilson Sonsini Goodrich & Rosati

(57) ABSTRACT

Integrated systems are provided for the production of higher hydrocarbon compositions, for example liquid hydrocarbon compositions, from methane using an oxidative coupling of methane system to convert methane to ethylene, followed by conversion of ethylene to selectable higher hydrocarbon products. Integrated systems and processes are provided that process methane through to these higher hydrocarbon products.

17 Claims, 6 Drawing Sheets

(51) Int. Cl.
  *C10G 50/00* (2006.01)
  *C07C 2/82* (2006.01)
  *F25J 3/02* (2006.01)

(52) U.S. Cl.
  CPC ........... *F25J 3/0219* (2013.01); *F25J 3/0233* (2013.01); *F25J 3/0238* (2013.01); *F25J 3/0257* (2013.01); *C10G 2300/1025* (2013.01); *F25J 2205/04* (2013.01); *F25J 2210/12* (2013.01); *F25J 2215/62* (2013.01); *F25J 2220/02* (2013.01); *F25J 2230/30* (2013.01); *F25J 2240/02* (2013.01); *F25J 2245/02* (2013.01); *Y02P 20/125* (2015.11)

(58) Field of Classification Search
  CPC .. F25J 2215/62; F25J 2220/02; F25J 2230/30; F25J 2240/02; F25J 2245/02; F25J 3/0219; F25J 3/0233; F25J 3/0238; F25J 3/0257; C10G 2300/1025; C10G 50/00
  See application file for complete search history.

(56) References Cited

U.S. PATENT DOCUMENTS

| | | | |
|---|---|---|---|
| 2,673,221 A | 3/1954 | Schrader et al. |
| 2,943,125 A | 6/1960 | Ziegler et al. |
| 3,128,317 A | 4/1964 | Arkell et al. |
| 3,413,817 A | 12/1968 | Kniel |
| 3,459,678 A | 8/1969 | Hagemeyer et al. |
| 3,584,071 A | 6/1971 | Mcnulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,862,257 A | 1/1975 | Buben et al. |
| 3,900,526 A | 8/1975 | Johnson et al. |
| 3,931,349 A | 1/1976 | Kuo |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,314,090 A | 2/1982 | Shewbart et al. |
| 4,329,530 A | 5/1982 | Irvine et al. |
| 4,367,353 A | 1/1983 | Inglis |
| 4,375,566 A | 3/1983 | Kawamata et al. |
| 4,433,185 A | 2/1984 | Tabak |
| 4,440,956 A | 4/1984 | Couvillion |
| 4,465,887 A | 8/1984 | Schammel |
| 4,481,305 A | 11/1984 | Jorn et al. |
| 4,551,438 A | 11/1985 | Miller |
| 4,552,644 A | 11/1985 | Johnson et al. |
| 4,567,307 A | 1/1986 | Jones et al. |
| 4,629,718 A | 12/1986 | Jones et al. |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,814,539 A | 3/1989 | Jezl et al. |
| 4,822,477 A | 4/1989 | Avidan et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,882,400 A | 11/1989 | Dumain et al. |
| 4,895,823 A | 1/1990 | Kolts et al. |
| 4,900,347 A | 2/1990 | McCue et al. |
| 4,935,568 A | 6/1990 | Harandi et al. |
| 4,939,312 A | 7/1990 | Baerns et al. |
| 4,966,874 A | 10/1990 | Young et al. |
| 5,012,028 A | 4/1991 | Gupta et al. |
| 5,034,565 A | 7/1991 | Harandi et al. |
| 5,057,638 A | 10/1991 | Sweeney |
| 5,080,872 A | 1/1992 | Jezl et al. |
| 5,118,898 A | 6/1992 | Tyler et al. |
| 5,132,472 A | 7/1992 | Durante et al. |
| 5,137,862 A | 8/1992 | Mackrodt et al. |
| 5,179,056 A | 1/1993 | Bartley |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,336,825 A * | 8/1994 | Choudhary ............... C07C 2/76 585/500 |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,473,027 A | 12/1995 | Batchelor et al. |
| 5,523,493 A | 6/1996 | Cameron et al. |
| 5,599,510 A | 2/1997 | Kaminsky et al. |
| 5,633,422 A | 5/1997 | Murray |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,715,657 A | 2/1998 | Mondani et al. |
| 5,723,713 A | 3/1998 | Maunders |
| 5,736,107 A | 4/1998 | Inomata et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,830,822 A | 11/1998 | Euzen |
| 5,849,973 A | 12/1998 | Van Der Vaart |
| 5,856,257 A | 1/1999 | Freeman et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,936,135 A | 8/1999 | Choudhary et al. |
| 6,013,851 A | 1/2000 | Verrelst et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,146,549 A | 11/2000 | Mackay et al. |
| 6,153,149 A | 11/2000 | Rabitz et al. |
| 6,158,149 A | 12/2000 | Rudy |
| 6,221,986 B1 | 4/2001 | Commereuc et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | Kibby |

(56) References Cited

U.S. PATENT DOCUMENTS

| | | |
|---|---|---|
| 6,713,657 B2 | 3/2004 | Miller |
| 6,726,850 B1 | 4/2004 | Reyes et al. |
| 6,759,562 B2 | 7/2004 | Gartside et al. |
| 6,764,602 B2 | 7/2004 | Shutt et al. |
| 6,768,035 B2 | 7/2004 | Mathur et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,157,612 B2 | 1/2007 | Ewert et al. |
| 7,164,052 B2 | 1/2007 | Carati et al. |
| 7,183,451 B2 | 2/2007 | Gattis et al. |
| 7,196,238 B2 | 3/2007 | Nurminen et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,781,636 B2 | 8/2010 | Iaccino et al. |
| 7,795,490 B2 | 9/2010 | Iaccino et al. |
| 7,838,710 B2 | 11/2010 | Ryu |
| 7,879,119 B2 | 2/2011 | Abughazaleh et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,021,620 B2 | 9/2011 | Nicholas et al. |
| 8,080,215 B2 | 12/2011 | Taheri et al. |
| 8,119,848 B2 | 2/2012 | Cross et al. |
| 8,129,305 B2 | 3/2012 | Bagherzadeh et al. |
| 8,153,851 B2 | 4/2012 | Gartside et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,399,527 B1 | 3/2013 | Brown et al. |
| 8,399,726 B2 | 3/2013 | Chinta et al. |
| 8,552,236 B2 | 10/2013 | Iaccino et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,912,109 B2 | 12/2014 | Chinta et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,512,047 B2 | 12/2016 | Nyce et al. |
| 2003/0045761 A1 | 3/2003 | Kuechler et al. |
| 2003/0094398 A1 | 5/2003 | Porter et al. |
| 2003/0189202 A1 | 10/2003 | Li et al. |
| 2004/0220053 A1 | 11/2004 | Bagherzadeh et al. |
| 2005/0065391 A1 | 3/2005 | Gattis et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0283780 A1 | 12/2006 | Spivey et al. |
| 2007/0027030 A1 | 2/2007 | Cheung et al. |
| 2007/0083073 A1 | 4/2007 | Bagherzadeh et al. |
| 2008/0141713 A1 | 6/2008 | Verma |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian, Jr. et al. |
| 2010/0003179 A1 | 1/2010 | Katusic et al. |
| 2010/0191031 A1 | 7/2010 | Sundaram |
| 2010/0197986 A1 | 8/2010 | Midorikawa et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0124488 A1 | 5/2011 | Neltner et al. |
| 2011/0189559 A1 | 8/2011 | De Miranda et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2012/0041246 A1 | 2/2012 | Scher et al. |
| 2012/0065412 A1 | 3/2012 | Abdallah et al. |
| 2012/0129690 A1 | 5/2012 | Larcher et al. |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2013/0023079 A1 | 1/2013 | Kang et al. |
| 2013/0023709 A1 | 1/2013 | Cizeron et al. |
| 2013/0040806 A1 | 2/2013 | Dismukes et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2014/0012053 A1 | 1/2014 | Iyer et al. |
| 2014/0018589 A1 | 1/2014 | Iyer et al. |
| 2014/0107385 A1 | 4/2014 | Schammel et al. |
| 2014/0121433 A1 | 5/2014 | Cizeron et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0181877 A1 | 6/2014 | Haykinson et al. |
| 2014/0235911 A1 | 8/2014 | Laha |
| 2014/0274671 A1 | 9/2014 | Schammel et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0232395 A1 | 8/2015 | Nyce et al. |
| 2015/0329438 A1 | 11/2015 | Nyce et al. |
| 2015/0329439 A1 | 11/2015 | Nyce et al. |
| 2016/0200643 A1 | 7/2016 | Nyce et al. |
| 2016/0368834 A1 | 12/2016 | Nyce et al. |

FOREIGN PATENT DOCUMENTS

| | | |
|---|---|---|
| CN | 101224432 A | 7/2008 |
| CN | 101387019 A | 3/2009 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |

(56) References Cited

FOREIGN PATENT DOCUMENTS

| | | |
|---|---|---|
| DE | 4338416 C1 | 4/1995 |
| EP | 0 253 522 A2 | 1/1988 |
| EP | 0608447 A1 | 8/1994 |
| EP | 0634211 A1 | 1/1995 |
| EP | 0722822 A1 | 7/1996 |
| EP | 0716064 B1 | 7/1998 |
| EP | 1110930 A1 | 6/2001 |
| EP | 1 632 467 A1 | 3/2006 |
| EP | 1 749 807 A1 | 2/2007 |
| EP | 1749806 B1 | 10/2008 |
| FR | 649429 A | 12/1928 |
| GB | 733336 A | 7/1955 |
| GB | 2191212 A * 12/1987 ............... C07C 2/76 | |
| JP | 2005-161225 A | 6/2005 |
| WO | WO 02/04119 A1 | 1/2002 |
| WO | 2004/033488 A2 | 4/2004 |
| WO | WO 2004/056479 A1 | 7/2004 |
| WO | WO 2004/103936 A1 | 12/2004 |
| WO | 2005/067683 A2 | 7/2005 |
| WO | 2007/130515 A2 | 11/2007 |
| WO | 2008/005055 A2 | 1/2008 |
| WO | 2008/014841 A1 | 2/2008 |
| WO | 2008/022147 A1 | 2/2008 |
| WO | 2008/073143 A2 | 6/2008 |
| WO | 2009/071463 A2 | 6/2009 |
| WO | WO 2009/074203 A1 | 6/2009 |
| WO | 2009/115805 A1 | 9/2009 |
| WO | WO 2011/008464 A1 | 1/2011 |
| WO | 2011/050359 A1 | 4/2011 |
| WO | WO 2011/041184 A2 | 4/2011 |
| WO | WO 2010/069488 A8 | 5/2011 |
| WO | 2011/149996 A2 | 12/2011 |
| WO | 2012/162526 A2 | 11/2012 |
| WO | 2013169462 A1 | 11/2013 |
| WO | 2013175204 A1 | 11/2013 |
| WO | WO 2013/177461 A2 | 11/2013 |
| WO | 2014044387 A1 | 3/2014 |
| WO | 2015000061 A1 | 1/2015 |
| WO | 2015003193 A2 | 1/2015 |
| WO | 2015021177 A1 | 2/2015 |

OTHER PUBLICATIONS

U.S. Appl. No. 13/479,767, filed May 24, 2012, Cizeron et al.
U.S. Appl. No. 13/689,611, filed Nov. 29, 2012, Zurcher et al.
U.S. Appl. No. 14/099,614, filed Dec. 6, 2013, Nyce et al.
U.S. Appl. No. 14/212,435, filed Mar. 14, 2014, Schammel et al.
U.S. Appl. No. 14/553,795, filed Nov. 25, 2014, Cizeron et al.
U.S. Appl. No. 61/564,836, filed Nov. 29, 2011, Nyce et al.
U.S. Appl. No. 61/651,485, filed May 24, 2012, Schammel et al.
U.S. Appl. No. 61/669,523, filed Jul. 9, 2012, Iyer et al.
U.S. Appl. No. 61/773,669, filed Mar. 6, 2013, Iyer et al.
U.S. Appl. No. 61/791,312, filed May 15, 2013, Schammel et al.
U.S. Appl. No. 61/794,486, filed Mar. 15, 2013, Schammel et al.
U.S. Appl. No. 62/050,729, filed Sep. 15, 2014, Rafique et al.
U.S. Appl. No. 62/073,478, filed Oct. 31, 2014, Rafique et al.
Bollmann, et al. Ethylene tetramerization: a new route to produce 1-octene in exceptionally high selectivities. J Am Chem Soc. Nov. 17, 2004;126(45):14712-3.
Carter, et al. High activity ethylene trimerisation catalysts based on diphosphine ligands. Chem Commun (Camb). Apr. 21, 2002;(8):858-9.
Chemsystems PERP Report Ethylene Oxide/Ethylene Glycol 2005.
Choudhary, et al. Microporous and Mesoporous Materials. 2001. 253-267.
International search report and written opinion dated Mar. 6, 2014 for PCT/US2013/042480.
International search report and written opinion dated Nov. 1, 2013 for PCT/US2013/049742.
International search report dated Mar. 19, 2014 for PCT Application No. US2013/073657.
Knuuttila, et al. Advanced Polyethylene Technologies—Controlled Material Properties. Long Term Properties of Polyolefins Advances in Polymer Science vol. 169, 2004, pp. 13-28.
Li, et al. Energy and Fuels. 2008, 22: 1897-1901.
Natural Gas Spec Sheet, 2003, prepared by Florida Power and Light Company.
Nexant/Chemsystems HDPE Report, PERP 09/10-3, Jan. 2011.
Nyce, et al. Integrated processes and systems for conversion of methane to multiple high hydrocarbon products. U.S. Appl. No. 14/099,614, filed on Dec. 6, 2013, 67 pages.
Office action dated Oct. 23, 2014 for U.S. Appl. No. 13/739,954.
Olah, G. Hydrocarbon Chemistry. 2nd Edition, John Wiley & Sons, 2003.
Zhang, Q. Journal of Natural Gas Chem., 12:81, 2003.
U.S. Appl. No. 14/591,850, filed Jan. 7, 2015, Nyce et al.
U.S. Appl. No. 14/592,668, filed Jan. 8, 2015, Rafique et al.
Barrett, et al. The determination of pore volume and area distributions in porous substances—Compuatations from nitrogen isotherms. J. Am. Chem. Soc., 1951, vol. 73, pp. 373-380.
Botella, et al. Effect of Potassium Doping on the Catalytic Behavior of Mo-V-Sb Mixed Oxide Catalysts in the Oxidation of Propane to Acrylic Acid. Catalysis Letters, Sep. 2003, vol. 89, Issue 3-4, pp. 249-253.
Chen, et al. M2 Forming—A Process for Aromatization of Light Hydrocarbons. Ind. Eng. Chem. Process. Des. Dev. 1986, 25, 151-155.
Li, et al. Combined Single-Pass Conversion of Methane Via Oxidative Coupling and Dehydroaromatization. Catalysis Letters, Sep. 2003, vol. 89, Issue 3-4, pp. 275-279.
Nielsen, et al. Treat LPGs with amines. Hydrocarbon Process 79 (1997): 49-59.
Saito, et al. Dehydrogenation of Propane Over a Silica-Supported Gallium Oxide Catalyst. Catalysis Letters, Sep. 2003, vol. 89, Issue 3-4, pp. 213-217.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Xu, et al. Maximise ethylene gain and acetylene selective hydrogenation efficiency. Petroleum technology quarterly 18.3 (2013): 39-42.
Zhou. BP-UOP Cyclar Process. Handbook of Petroleum Refining Processes, The McGraw-Hill Companies (2004), pp. 2.29-2.38.
Ding, X et al. "Effect of acid density of HZSM-5 on the oligomerization of ethylene in FCC dry gas" J Nat Gas Chem (2009) 18:156-160.
Haag, W.O. et al. "Aromatics, Light Olefins and Gasoline from Methanol: Mechanistic Pathways with ZSM-5 Zeolite Catalyst" J Mol Catalysis (1982) 17:161-169.
International search report and written opinion dated Jun. 26, 2015 for PCT Application No. US2015/010525.
Lunsford, J.H. "Catalytic conversion of methane to more useful chemicals and fuels: a challenge for the 21st century" Catalysis Today (2000) 63:165-174.
Morgan, C.R. et al. "Gasoline from Alcohols" Ind Eng Chem Prod Res Dev (1981) 20:185-190.
Nyce, G. et al. "Ethylene-to-Liquids Systems and Methods" U.S. Appl. No. 14/789,917, filed Jul. 1, 2015.
Nyce, G. et al. "Ethylene-to-Liquids Systems and Methods" U.S. Appl. No. 14/789,936 filed Jul. 1, 2015.
Nyce, G. et al. "Ethylene-to-Liquids Systems and Methods" U.S. Appl. No. 14/789,957 filed Jul. 1, 2015.
Tabak, S.A. et al. "Conversion of Methanol over ZSM-5 to Fuels and Chemicals" Cat Today (1990) 307-327.
Office action dated Sep. 11, 2015 for U.S. Appl. No. 14/789,917.
Office Action dated Sep. 23, 2015 for U.S. Appl. No. 14/789,936.
Notice of allowance dated Jan. 20, 2016 for U.S. Appl. No. 14/789,936.
Notice of allowance dated Jan. 21, 2016 for U.S. Appl. No. 14/789,917.
Notice of allowance dated Dec. 30, 2015 for U.S. Appl. No. 14/789,957.

(56) References Cited

OTHER PUBLICATIONS

Guo et al., "Current Status and Some Perspectives of Rare Earth Catalytic Materials," *Journal of The Chinese Rare Earth Society* 25(1):1-15, Feb. 2007.

Ling et al., "Preparation of $Ag_{core}Au_{shell}$ Nanowires and Their Surface Enhanced Raman Spectroscopic Studies," *Acta Chimica Sinica* 65(9):779-784, 2007.

Niu et al., "Preparation and Characterization of $La_2O_2CO_3$ Nanowires with High Surface Areas," *Journal of the Chinese Rare Earth Society* 23(Spec. Issue):33-36, Dec. 2005.

Tong et al., "Development Strategy Research of Downstream Products of Ethene in Tianjin," *Tianjin Economy*, pp. 37-40, 1996.

Yu et al., "Oxidative Coupling of Methane Over Acceptor-doped $SrTiO_3$: Correlation Between p-type Conductivity and $C_2$ Selectivity and $C_2$ Yield," *Journal of Catalysis* 13(5):338-344, 1992.

Zhao, "Technologies and Catalysts for Catalytic Preparation of Ethene," *Industrial Catalysis* 12(Supplement):285-289, 2004.

Mleczko et al., "Catalytic oxidative coupling of methane—reaction engineering aspects and process schemes," *Fuel Processing Technology* 42:217-248, 1995.

Co-pending U.S. Appl. No. 15/076,436, filed Mar. 21, 2016.

International preliminary report on patentability dated Jul. 21, 2016 for PCT Application No. US2015/010525.

Notice of allowance dated Jul. 29, 2016 for U.S. Appl. No. 15/076,512.

Office action dated Apr. 21, 2016 for U.S. Appl. No. 15/076,512.

"Autothermal Partial Oxidative Coupling of Methane," IP.com, Prior Art Database Technical Disclosure, Jul. 29, 2008, 5 pages.

Cavani et al., "Oxidative dehydrogenation of ethane and propane: How far from commercial implementation?," *Catalysis Today* 127: 113-131, 2007.

Choudhary et al., "Aromatization of dilute ethylene over Ga-modified ZSM-5 type zeolite catalysts," *Microporous and Mesoporous Materials* 47: 253-267, 2001.

Choudhary et al., "Oxidative conversion of methane/natural gas into higher hydrocarbons," *Catalysis Surveys from Asia* 8(1): 15-25, 2004.

Choudhary et al., "Surface Basicity and Acidity of Alkaline Earth-Promoted $La_2O_3$ Catalysts and Their Performance in Oxidative Coupling of Methane," *J. Chem. Technol. Biotechnol.* 72: 125-130, 1998.

Christopher et al., "Engineering Selectivity in Heterogeneous Catalysis: Ag Nanowires as Selective Ethylene Epoxidation Catalysts," *J. Am. Chem. Soc.* 130: 11264-11265, 2008.

Cizeron et al., "Catalysts for Petrochemical Catalysis," U.S. Appl. No. 61/489,651, filed May 24, 2011, 86 pages.

Cizeron et al., "Catalysts for Petrochemical Catalysis," U.S. Appl. No. 61/564,832, filed Nov. 29, 2011, 178 pages.

Cizeron et al., "Catalytic Forms and Formulations," U.S. Appl. No. 13/901,319, filed May 23, 2013, 132 pages.

Débart et al., "α-$MnO_2$ Nanowires: A Catalyst for the $O_2$ Electrode in Rechargeable Lithium Batteries," *Angew. Chem. Int. Ed.* 47: 4521-4524, 2008.

Enger et al., "A review of catalytic partial oxidation of methane to synthesis gas with emphasis on reaction mechanisms over transition metal catalysts," *Applied Catalysis A: General* 346: 1-27, 2008.

Gao et al., "A study on methanol stream reforming to $CO_2$ and $H_2$ over the $La_2CuO_4$ nanofiber catalyst," *Journal of Solid State Chemistry* 181: 7-13, 2008.

Gao et al., "The direct decomposition of NO over the $La_2CuO_4$ nanofiber catalyst," *Journal of Solid State Chemistry* 181: 2804-2807, 2008.

Huang et al., "Exploiting shape effects of $La_2O_3$ nanocrystals for oxidative coupling of methane reaction," *Nanoscale* 5(22): 10844-10848, 2013.

Huang et al., "Exploiting Shape Effects of $La_2O_3$ Nanocrystals for Oxidative Coupling of Methane Reaction," *Nanoscale—Electronic Supplementary Material*, 2013, 7 pages.

Keller et al., "Synthesis of Ethylene via Oxidative Coupling of Methane," *Journal of Catalysis* 73: 9-19, 1982.

Kuang et al., "Grafting of PEG onto lanthanum hydroxide nanowires," *Materials Letters* 62: 4078-4080, 2008.

Labinger, "Oxidative Coupling of Methane: An Inherent Limit to Selectivity?," *Catalysis Letters* 1: 371-376, 1988.

Liu et al., "A novel $Na_2WO_4$-Mn/SiC monolithic foam catalyst with improved thermal properties for the oxidative coupling of methane," *Catalysis Communications* 9: 1302-1306, 2008.

Lunsford, "The Catalytic Oxidative Coupling of Methane," *Angew. Chem. Int. Ed. Engl.* 34: 970-980, 1995.

Neltner et al., "Production of Hydrogen Using Nanocrystalline Protein-Templated Catalysts on M13 Phage," *ACS Nano* 4(6): 3227-3235, 2010.

Neltner, "Hybrid Bio-templated Catalysts," Submitted to the Department of Materials Science and Engineering in partial fulfillment of the requirements for the degree of Doctor of Philosophy in Material Science and Engineering at the Massachusetts Institute of Technology, Jun. 2010, 156 pages.

Nyce et al., "Polymer Templated Nanowire Catalysts," U.S. Appl. No. 61/564,836, filed Nov. 29, 2011, 317 pages.

Pak et al., "Elementary Reactions in the Oxidative Coupling of Methane over $Mn/Na_2WO_4/SiO_2$ and $Mn/Na_2WO_4/MgO$ Catalysts," *Journal of Catalysts* 179: 222-230, 1998.

Qiu et al., "Steady-state conversion of methane to aromatics in high yields using an integrated recycle reaction system," *Catalysis Letters* 48:11-15, 1997.

Schammel et al., "Catalysts for Petrochemical Catalysis," U.S. Appl. No. 61/794,486, filed Mar. 15, 2013, 217 pages.

Schammel et al., "Oxidative Coupling of Methane Systems and Methods," U.S. Appl. No. 13/900,898, filed May 23, 2013, 201 pages.

Schweer et al., "OCM in a fixed-bed reactor: limits and perspectives," *Catalysis Today* 21: 357-369, 1994.

Somorjai et al., "High technology catalysts towards 100% selectivity—Fabrication, characterization and reaction studies," *Catalysis Today* 100: 201-215, 2005.

Takanabe et al., "Mechanistic Aspects and Reaction Pathways for Oxidative Coupling of Methane on $Mn/Na_2WO_4/SiO_2$ Catalysts," *J. Phys. Chem. C* 113: 10131-10145, 2009.

Takanabe et al., "Rate and Selectivity Enhancements Mediated by OH Radicals in the Oxidative Coupling of Methane Catalyzed by $Mn/Na_2WO_4/SiO_2$," *Angew. Chem. Int. Ed.* 47: 7689-7693, 2008.

Trautmann et al., "Cryogenic Technology for Nitrogen Rejection from Variable Content Natural Gas," Presented at the XIV Covencion Internacional de Gas, Caracas, Venezuela, May 10-12, 2000, 13 pages.

Wang et al., "Autothermal oxidative coupling of methane on the $SrCO_3/Sm_2O_3$ catalysts," *Catalysis Communications* 10: 807-810, 2009.

Wang et al., "Comparative study on oxidation of methane to ethane and ethylene over $Na_2WO_4$-$Mn/SiO_2$ catalysts prepared by different methods," *Journal of Molecular Catalysis A: Chemical* 245: 272-277, 2006.

Wang et al., "Low-temperature selective oxidation of methane to ethane and ethylene over $BaCO_3/La_2O_3$ catalysts prepared by urea combustion method," *Catalysis Communications* 7: 59-63, 2006.

Wong et al., "Oxidative Coupling of Methane over Alkali Metal Oxide Promoted $La_2O_3/BaCO_3$ Catalysts," *J. Chem. Tech. Biotechnol.* 65: 351-354, 1996.

Yang et al., "Anisotropic synthesis of boat-shaped core-shell Au-Ag nanocrystals and nanowires," *Nanotechnology* 17: 2304-2310, 2006.

Zhou et al., "Functionalization of lanthanum hydroxide nanowires by atom transfer radical polymerization," *Nanotechnology* 18: 405704, 2007. (7 pages).

Zimmermann et al., "Ethylene," *Ulmann's Encyclopedia of Industrial Chemistry*, Wiley-VCH Verlag GmbH & Co. KGaA, Weinham, Germany, 2009, 66 pages.

Zurcher et al., "Nanowire Catalysts," U.S. Appl. No. 61/564,834, filed Nov. 29, 2011, 367 pages.

(56) References Cited

OTHER PUBLICATIONS

Zurcher et al., "Nanowire Catalysts," U.S. Appl. No. 61/651,399, filed May 24, 2012, 406 pages.
Co-pending U.S. Appl. No. 15/335,183, filed Oct. 26, 2016.

* cited by examiner

INTEGRATED PROCESSES AND SYSTEMS FOR CONVERSION OF METHANE TO MULTIPLE HIGHER HYDROCARBON PRODUCTS

CROSS-REFERENCE

This application claims the benefit of U.S. Provisional Application No. 61/734,865, filed on Dec. 7, 2012, which is incorporated herein by reference in its entirety.

BACKGROUND

Technical Field

This invention is generally related to novel hydrocarbon processes and systems for the conversion of methane into various higher hydrocarbons.

Description of the Related Art

The chemicals and fuels industry has evolved and developed over time based upon the relative abundance and highly cost effective production and refining of crude oil. In particular, inexpensive crude oil and historically proven refining technologies have produced large numbers of high value chemicals and chemical precursors that are used in virtually every aspect of human society, from building materials, consumer products, automobiles, packaging, sheeting, fabrics, etc. Likewise, crude oil and its refined products are used extensively as fuels and fuel blendstocks for driving cars, trains, boats and airplanes, etc. Despite the historical economics of crude oil refining, geo-political and geo-economic forces have tended to impact the availability and cost of crude oil. In addition, the expense of recovering oil and its relative decrease in abundance has increased its cost over time.

Natural gas, on the other hand, is generally relatively abundant, and particularly abundant in relatively stable regions, e.g., North America, Eastern Europe and China. However, natural gas suffers from difficulties associated with moving high volumes of gas across vast expanses, requiring substantial infrastructure costs, e.g., to build and manage complex pipelines. Likewise, to date, technologies for the production of the aforementioned chemicals and fuels from natural gas have not proven to be economical under normal market conditions. It is therefore desirable to provide processes and systems that can start with natural gas, and particularly methane in natural gas, for the production of higher hydrocarbon materials, and particularly easily transportable liquid compositions, for use as chemicals, chemical precursors, liquid fuels and fuel blendstocks, and the like. The present invention meets these and other related needs.

BRIEF SUMMARY

The present invention is generally directed to the production of high value olefinic and other hydrocarbon products from abundant feed materials, such as methane in natural gas. In particular, the invention provides, in certain aspects, integrated and selectable processes and systems for the production of a wide range of different liquid hydrocarbon compositions from methane, which products can be used in chemical processes, or as fuels or fuel blends.

Embodiments of the invention generally provide integrated systems and processes for the conversion of methane to ethylene and subsequent conversion of ethylene to one or more different higher hydrocarbon products, and particularly liquid hydrocarbon products.

In one embodiment, the invention provides a method of producing a plurality of hydrocarbon products, the method comprising:

introducing methane and a source of oxidant into an OCM reactor system capable of converting methane to ethylene at reactor inlet temperatures of between about 450° C. and 600° C. and reactor pressures of between about 15 psig and 125 psig, with C2+ selectivity of at least 50%, under conditions for the conversion of methane to ethylene;

converting methane to a product gas comprising ethylene;

introducing separate portions of the product gas into at least first and second integrated ethylene conversion reaction systems, each integrated ethylene conversion reaction system being configured for converting ethylene into a different higher hydrocarbon product; and converting the ethylene into different higher hydrocarbon products.

In still other embodiments, the invention provides a method of producing a plurality of liquid hydrocarbon products, the method comprising:

converting methane to a product gas comprising ethylene using a catalytic reactor process; and contacting separate portions of the product gas with at least two discrete catalytic reaction systems selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

Other embodiments of the present disclosure are directed to a processing system, the processing system comprising:

an OCM reactor system comprising an OCM catalyst, the OCM reactor system being fluidly connected at an input, to a source of methane and a source of oxidant;

at least first and second catalytic ethylene conversion reactor systems, the first catalytic ethylene reactor system being configured to convert ethylene to a first higher hydrocarbon, and the second catalytic ethylene reactor system being configured to convert ethylene to a second higher hydrocarbon different from the first higher hydrocarbon; and a selective coupling between the OCM reactor system and the first and second catalytic ethylene reactor systems configured to selectively direct a portion or all of the product gas to each of the first and second catalytic ethylene reactor systems.

These and other aspects of the invention will be apparent upon reference to the following detailed description. To this end, various references are set forth herein which describe in more detail certain background information, procedures, reactors and/or catalysts, and are each hereby incorporated by reference in their entirety.

BRIEF DESCRIPTION OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION

I. General

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The present invention is generally directed to novel processes and systems for use in the production of hydrocarbon compositions. These processes and systems may be characterized in that they derive the hydrocarbon compositions from ethylene that is, in turn, derived from methane, for example as is present in natural gas. The disclosed processes and systems are typically further characterized in that the process for conversion of methane to ethylene is integrated with one or more processes or systems for converting ethylene to one or more higher hydrocarbon products, which, in some embodiments, comprise liquid hydrocarbon compositions. By converting the methane present in natural gas to a liquid material, one can eliminate one of the key hurdles involved in exploitation of the world's vast natural gas reserves, namely transportation. In particular, exploitation of natural gas resources traditionally has required extensive, and costly pipeline infrastructures for movement of gas from the wellhead to its ultimate destination. By converting that gas to a liquid material, more conventional transportation systems become available, such as truck, rail car, tanker ship, and the like.

Figure 1:
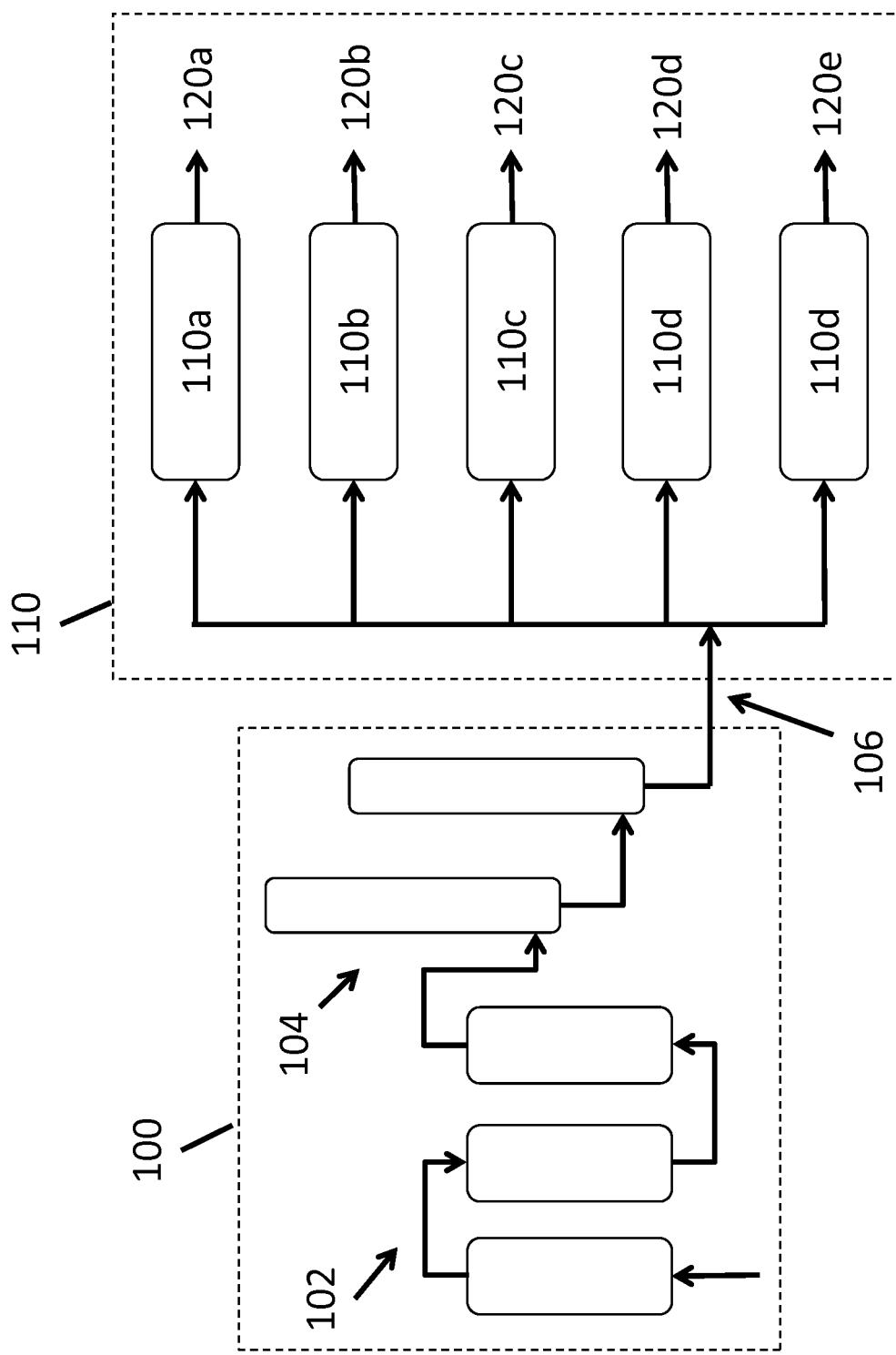
FIG. 1 schematically illustrates a general integrated process flow of the invention.

In further embodiments, processes and systems of the invention include multiple (i.e., two or more) ethylene conversion process paths integrated into the overall processes or systems, in order to produce multiple different higher hydrocarbon compositions from the single original methane source. Further advantages are gained by providing the integration of these multiple conversion processes or systems in a switchable or selectable architecture whereby a portion or all of the ethylene containing product of the methane to ethylene conversion system is selectively directed to one or more different process paths, for example two, three, four, five or more different process paths to yield as many different products. This overall process flow is schematically illustrated in FIG. 1. As shown, an oxidative coupling of methane ("OCM") reactor system 100 is schematically illustrated that includes an OCM reactor train 102 coupled to a OCM product gas separation train 104, such as a cryogenic separation system. The ethylene rich effluent (shown as arrow 106) from the separation train 104 is shown being routed to multiple different ethylene conversion reactor systems and processes 110, e.g., ethylene conversion systems 110a-110e, which each produce different hydrocarbon products, e.g., products 120a-120e.

As noted, the fluid connection between the OCM reactor system 100 and each of the different ethylene conversion systems 110a-110e, is a controllable and selective connection in some embodiments, e.g., a valve and control system, that can apportion the output of the OCM reactor system to one, two, three, four, five or more different ethylene conversion systems. Valve and piping systems for accomplishing this may take a variety of different forms, including valves at each piping junction, multiport valves, multivalved manifold assemblies, and the like.

As used herein, and unless the context dictates otherwise, the following terms have the meanings as specified below.

"Catalyst" means a substance that alters the rate of a chemical reaction. A catalyst may either increase the chemical reaction rate (i.e. a "positive catalyst") or decrease the reaction rate (i.e. a "negative catalyst"). Catalysts participate in a reaction in a cyclic fashion such that the catalyst is cyclically regenerated. "Catalytic" means having the properties of a catalyst.

"Nanowire" means a nanowire structure having at least one diameter on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D.

"Polycrystalline nanowire" means a nanowire having multiple crystal domains. Polycrystalline nanowires generally have different morphologies (e.g. bent vs. straight) as compared to the corresponding "single-crystalline" nanowires.

"Effective length" of a nanowire means the shortest distance between the two distal ends of a nanowire as measured by transmission electron microscopy (TEM) in bright field mode at 5 keV. "Average effective length" refers to the average of the effective lengths of individual nanowires within a plurality of nanowires.

"Actual length" of a nanowire means the distance between the two distal ends of a nanowire as traced through the backbone of the nanowire as measured by TEM in bright field mode at 5 keV. "Average actual length" refers to the average of the actual lengths of individual nanowires within a plurality of nanowires.

The "diameter" of a nanowire is measured in an axis perpendicular to the axis of the nanowire's actual length (i.e. perpendicular to the nanowires backbone). The diameter of a nanowire will vary from narrow to wide as measured at different points along the nanowire backbone. As used herein, the diameter of a nanowire is the most prevalent (i.e. the mode) diameter.

The "ratio of effective length to actual length" is determined by dividing the effective length by the actual length. A nanowire having a "bent morphology" will have a ratio of effective length to actual length of less than one as described in more detail herein. A straight nanowire will have a ratio of effective length to actual length equal to one.

"Inorganic" means a substance comprising a metal element or semi-metal element. In certain embodiments, inorganic refers to a substance comprising a metal element. An inorganic compound can contain one or more metals in its elemental state, or more typically, a compound formed by a metal ion ($M^{n+}$, wherein n 1, 2, 3, 4, 5, 6 or 7) and an anion ($X^{m-}$, m is 1, 2, 3 or 4), which balance and neutralize the positive charges of the metal ion through electrostatic interactions. Non-limiting examples of inorganic compounds include oxides, hydroxides, halides, nitrates, sulfates, carbonates, phosphates, acetates, oxalates, and combinations thereof, of metal elements. Other non-limiting examples of inorganic compounds include $Li_2CO_3$, $Li_2PO_4$, $LiOH$, $Li_2O$, $LiCl$, $LiBr$, $LiI$, $Li_2C_2O_4$, $Li_2SO_4$, $Na_2CO_3$, $Na_2PO_4$, $NaOH$, $Na_2O$, $NaCl$, $NaBr$, $NaI$, $Na_2C_2O_4$, $Na_2SO_4$, $K_2CO_3$, $K_2PO_4$, $KOH$, $K_2O$, $KCl$, $KBr$, $KI$, $K_2C_2O_4$, $K_2SO_4$, $Cs_2CO_3$, $CsPO_4$, $CsOH$, $Cs_2O$, $CsCl$, $CsBr$, $CsI$, $CsC_2O_4$, $CsSO_4$, $Be(OH)_2$, $BeCO_3$, $BePO_4$, $BeO$, $BeCl_2$, $BeBr_2$, $BeI_2$, $BeC_2O_4$. $BeSO_4$, $Mg(OH)_2$, $MgCO_3$, $MgPO_4$, $MgO$, $MgCl_2$, $MgBr_2$, $MgI_2$, $MgC_2O_4$. $MgSO_4$, $Ca(OH)_2$, $CaO$, $CaCO_3$, $CaPO_4$, $CaCl_2$, $CaBr_2$, $CaI_2$, $Ca(OH)_2$, $CaC_2O_4$, $CaSO_4$, $Y_2O_3$, $Y_2(CO_3)_3$, $Y_2(PO_4)_3$, $Y(OH)_3$, $YCl_3$, $YBr_3$, $YI_3$, $Y_2(C_2O4)_3$, $Y_2(SO4)_3$, $Zr(OH)_4$, $Zr(CO_3)_2$, $Zr(PO_4)_2$, $ZrO(OH)_2$, $ZrO2$, $ZrCl_4$, $ZrBr_4$, $ZrI_4$, $Zr(C_2O_4)_2$, $Zr(SO_4)_2$, $Ti(OH)_4$, $TiO(OH)_2$, $Ti(CO_3)_2$, $Ti(PO_4)_2$, $TiO2$, $TiCl_4$, $TiBr_4$, $TiI_4$, $Ti(C_2O_4)_2$, $Ti(SO_4)_2$, $BaO$, $Ba(OH)_2$, $BaCO_3$, $BaPO_4$, $BaCl_2$, $BaBr_2$, $BaI_2$, $BaC_2O_4$, $BaSO_4$, $La(OH)_3$, $La_2(CO_3)_3$, $La_2(PO_4)_3$, $La_2O_3$, $LaCl_3$, $LaBr_3$, $LaI_3$, $La_2(C_2O_4)_3$, $La_2(SO_4)_3$, $Ce(OH)_4$, $Ce(CO_3)_2$, $Ce(PO_4)_2$, $CeO_2$, $Ce_2O_3$, $CeCl_4$, $CeBr_4$, $CeI_4$, $Ce(C_2O_4)_2$, $Ce(SO_4)_2$, $ThO_2$, $Th(CO_3)_2$, $Th(PO_4)_2$, $ThCl_4$, $ThBr_4$, $ThI_4$, $Th(OH)_4$, $Th(C_2O_4)_2$, $Th(SO_4)_2$, $Sr(OH)_2$, $SrCO_3$, $SrPO_4$, $SrO$, $SrCl_2$, $SrBr_2$, $SrI_2$, $SrC_2O_4$, $SrSO_4$, $Sm_2O_3$, $Sm_2(CO_3)_3$, $Sm_2(PO_4)_3$, $SmCl_3$, $SmBr_3$, $SmI_3$, $Sm(OH)_3$, $Sm_2(CO3)_3$, $Sm_2(C_2O_3)_3$, $Sm_2(SO_4)_3$, $LiCa_2Bi_3O_4Cl_6$, $Na_2WO_4$, K/SrCoO$_3$, K/Na/SrCoO$_3$, Li/SrCoO$_3$, SrCoO$_3$, molybdenum oxides, molybdenum hydroxides, molybdenum carbonates, molybdenum phosphates, molybdenum chlorides, molybdenum bromides, molybdenum iodides, molybdenum oxalates, molybdenum sulfates, manganese oxides, manganese chlorides, manganese bromides, manganese iodides, manganese hydroxides, manganese oxalates, manganese sulfates, manganese tungstates, vanadium oxides, vanadium carbonates, vanadium phosphates, vanadium chlorides, vanadium bromides, vanadium iodides, vanadium hydroxides, vanadium oxalates, vanadium sulfates, tungsten oxides, tungsten carbonates, tungsten phosphates, tungsten chlorides, tungsten bromides, tungsten iodides, tungsten hydroxides, tungsten oxalates, tungsten sulfates, neodymium oxides, neodymium carbonates, neodymium phosphates, neodymium chlorides, neodymium bromides, neodymium iodides, neodymium hydroxides, neodymium oxalates, neodymium sulfates, europium oxides, europium carbonates, europium phosphates, europium chlorides, europium bromides, europium iodides, europium hydroxides, europium oxalates, europium sulfates rhenium oxides, rhenium carbonates, rhenium phosphates, rhenium chlorides, rhenium bromides, rhenium iodides, rhenium hydroxides, rhenium oxalates, rhenium sulfates, chromium oxides, chromium carbonates, chromium phosphates, chromium chlorides, chromium bromides, chromium iodides, chromium hydroxides, chromium oxalates, chromium sulfates, potassium molybdenum oxides and the like.

"Salt" means a compound comprising negative and positive ions. Salts are generally comprised of cations and counter ions. Under appropriate conditions, e.g., the solution also comprises a template, the metal ion ($M^{n+}$) and the anion ($X^{m-}$) bind to the template to induce nucleation and growth of a nanowire of $M_mX_n$ on the template. "Anion precursor" thus is a compound that comprises an anion and a cationic counter ion, which allows the anion ($X^{m-}$) to dissociate from the cationic counter ion in a solution. Specific examples of the metal salt and anion precursors are described in further detail herein.

"Oxide" refers to a metal compound comprising oxygen. Examples of oxides include, but are not limited to, metal oxides ($M^{n+}$), metal oxyhalides ($M_xO_yX_z$), metal hydroxyhalides ($M_xOH_yX_z$), metal oxynitrates ($M_xO_y(NO_3)_z$), metal phosphates ($M_x(PO_4)_y$, metal oxycarbonates ($M_xO_y(CO_3)_z$), metal carbonates ($M_x(CO_3)_z$), metal sulfates ($M_x(SO_4)_z$), metal oxysulfates ($M_xO_y(SO_4)_z$), metal phosphates ($M_x(PO_4)_z$), metal acetates ($M_x(CH_3CO_2)_z$), metal oxalates ($M_x(C_2O_4)_z$), metal oxyhydroxides ($M_xO_y(OH)_z$), metal hydroxides ($M_x(OH)_z$), hydrated metal oxides ($M_xO_y).(H_2O)_z$ and the like, wherein X is independently, at each occurrence, fluoro, chloro, bromo or iodo, and x, y and z are independently numbers from 1 to 100.

"Mixed oxide" or "mixed metal oxide" refers to a compound comprising two or more oxidized metals and oxygen (i.e., $M1_xM2_yO_z$, wherein M1 and M2 are the same or different metal elements, O is oxygen and x, y and z are numbers from 1 to 100). A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 2, 3, 4, 5, 6 or more metal elements can be represented in an analogous manner. Mixed oxides also include oxy-hydroxides (e.g., $M_xO_yOH_z$, wherein M is a metal element, O is oxygen, x, y and z are numbers from 1 to 100 and OH is hydroxy). Mixed oxides may be represented herein as M1-M2, wherein M1 and M2 are each independently a metal element.

"Crystal domain" means a continuous region over which a substance is crystalline.

"Single-crystalline nanowires" or "mono-crystalline" means a nanowire having a single crystal domain.

"Dopant" or "doping agent" is an impurity added to or incorporated within a catalyst to optimize catalytic performance (e.g. increase or decrease catalytic activity). As compared to the undoped catalyst, a doped catalyst may increase or decrease the selectivity, conversion, and/or yield of a reaction catalyzed by the catalyst.

"OCM catalyst" refers to a catalyst capable of catalyzing the OCM reaction.

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), hafnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmistadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

"Actinides" include actinium (Ac), thorium (Th), protactinium (Pa), uranium (U), neptunium (Np), plutonium (Pu), americium (Am), curium (Cm), berklelium (Bk), californium (Cf), einsteinium (Es), fermium (Fm), mendelevium (Md), nobelium (No), and lawrencium (Lr).

"Rare earth" elements include Group 3, lanthanides and actinides.

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

"Semi-metal element" refers to an element selected from boron (B), silicon (Si), germanium (Ge), arsenic (As), antimony (Sb), tellurium (Te), and polonium (Po).

"Non-metal element" refers to an element selected from carbon (C), nitrogen (N), oxygen (O), fluorine (F), phosphorus (P), sulfur (S), chlorine (Cl), selenium (Se), bromine (Br), iodine (I), and astatine (At).

II. Methane to Ethylene Processes and Systems

As noted previously, the present invention includes processes and systems for production of various higher hydrocarbons (i.e., C3+) from ethylene, and particularly liquid hydrocarbon compositions. In particular aspects, the ethylene is itself derived from methane in a methane containing feedstock, such as natural gas. Production of ethylene from methane has been proposed through a number of different catalytic pathways, for example in some embodiments, the processes and systems of the invention convert methane to ethylene through OCM in an OCM reactor system. In certain embodiments, the ethylene produced in the OCM reactor system is charged to one or more ethylene conversion reactor systems where it is converted to a higher hydrocarbon, for example a different higher hydrocarbon in each of the ethylene conversion reactor systems.

Briefly, the OCM reaction is as follows: $2CH_4 + O_2 \rightarrow C_2H_4 + 2H_2O$. See, e.g., Zhang, Q., Journal of Natural Gas Chem., 12:81, 2003; Olah, G. "Hydrocarbon Chemistry", Ed. 2, John Wiley & Sons (2003). This reaction is exothermic ($\Delta H = -67$ kcals/mole) and has typically been shown to occur at very high temperatures (>700° C.). Although the detailed reaction mechanism is not fully characterized, experimental evidence suggests that free radical chemistry is involved. (Lunsford, J. Chem. Soc., Chem. Comm., 1991; H. Lunsford, Angew. Chem., Int. Ed. Engl., 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction. In particular, numerous publications from industrial and academic labs have consistently demonstrated characteristic performance of high selectivity at low conversion of methane, or low selectivity at high conversion (J. A. Labinger, Cat. Lett., 1:371, 1988). Limited by this conversion/selectivity threshold, no OCM catalyst has been able to exceed 20-25% combined C2 yield (i.e. ethane and ethylene), and more importantly, only approach these yields when operated at extremely high temperatures (>800° C.).

Despite the historical limitations of reported OCM processes, newer developments have provided OCM reactions, processes and systems that operate within economic and reasonable process windows. In particular, new catalysts, processes and reactor systems have been able to carry out OCM reactions at temperatures, pressures, selectivities and yields that are commercially attractive, and far more feasible from a process standpoint than previously reported reactions. See, e.g., U.S. patent application Ser. Nos. 13/115,082, 13/479,767, 13/689,611, 13/739,954, 13/900,898, 13/901,319, 61/773,669, 61/794,486, 61/909,840 and 61/669,523, the full disclosures of which are incorporated herein by reference in their entirety for all purposes.

As used herein, an OCM process or system typically employs one or more reactor vessels that contain an appropriate OCM catalyst material, typically in conjunction with additional system components. A variety of OCM catalysts have been described previously. See, e.g., U.S. Pat. Nos. 5,712,217, 6,403,523, and 6,576,803, the full disclosures of which are incorporated herein by reference in their entirety for all purposes. While these catalysts have been shown to catalyze an OCM reaction, for most of these catalysts, the reactions are carried out under conditions that are less practical or economical, i.e., at very high temperatures and/or pressures. Recently, novel catalysts have been developed that yield conversion and selectivity that enable economic methane conversion under practical operating conditions. These are described in, for example, Published U.S. Patent Application No. 2012-0041246, as well as patent application Ser. No. 13/479,767, filed May 24, 2012, and Ser. No. 13/689,611, filed Nov. 29, 2012, the full disclosures of each of which are incorporated herein by reference in their entirety for all purposes.

Accordingly, in one embodiment, the invention provides a method of producing a hydrocarbon product, the method comprising:

introducing methane and a source of oxidant into an OCM reactor system capable of converting methane to ethylene at reactor inlet temperatures of between about 450° C. and 600° C. and reactor pressures of between about 15 psig and 125 psig, with C2+ selectivity of at least 50%, under conditions for the conversion of methane to ethylene;

converting methane to a product gas comprising ethylene;

introducing at least a portion of the product gas into an integrated ethylene conversion reaction systems, the integrated ethylene conversion reaction system being configured for converting ethylene into a higher hydrocarbon product: and converting the ethylene into a higher hydrocarbon product.

In various embodiments of the above, the method is for producing a plurality of hydrocarbon products. Accordingly, in another embodiment, the invention provides a method of producing a plurality of hydrocarbon products, the method comprising:

introducing methane and a source of oxidant into an OCM reactor system capable of converting methane to ethylene at reactor inlet temperatures of between about 450° C. and 600° C. and reactor pressures of between about 15 psig and 125 psig, with C2+ selectivity of at least 50%, under conditions for the conversion of methane to ethylene;

converting methane to a product gas comprising ethylene;

introducing separate portions of the product gas into at least first and second integrated ethylene conversion reaction systems, each integrated ethylene conversion reaction system being configured for converting ethylene into a different higher hydrocarbon product: and converting the ethylene into different higher hydrocarbon products.

In certain embodiments of the foregoing methods, the integrated ethylene conversion systems are selected from selective and full range ethylene conversion systems.

In other embodiments the methods further comprise introducing a portion of the product gas into at least a third integrated ethylene conversion system. Other embodiments further comprise introducing a portion of the product gas into at least first, second, third and fourth integrated ethylene conversion systems.

In any of the foregoing methods, the integrated ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In some other embodiments, the integrated ethylene conversion systems are selected from LAO systems that produce one or more of 1-butene, 1-hexene, 1-octene and 1-decene. For example, in certain embodiments at least one of the LAO systems is configured for performing a selective LAO process.

In other embodiments of the foregoing, at least one of the integrated ethylene conversion systems comprises a full range ethylene oligomerization system configured for producing higher hydrocarbons in the range of C4 to C30.

In yet other embodiments, the OCM reactor system comprises nanowire OCM catalyst material. In some other embodiments, the product gas comprises less than 5 mol % of ethylene. For example, in certain embodiments, the product gas comprises less than 3 mol % of ethylene. In some other embodiments, the product gas further comprises one or more gases selected from $CO_2$, $CO$, $H_2$, $H_2O$, $C_2H_6$, $CH_4$ and C3+ hydrocarbons.

In other embodiments of the foregoing method, the method further comprises enriching the product gas for ethylene prior to introducing the separate portions of the product gas into the at least first and second integrated ethylene conversion reaction systems.

In some different embodiments, the foregoing method further comprises introducing an effluent gas from the first or second integrated ethylene conversion reaction systems into the OCM reactor system. For example, in some of these embodiments the method further comprises converting methane present in the effluent gas to ethylene and charging the ethylene to one or more of the aforementioned integrated ethylene conversion systems.

In various different embodiments, the invention is directed to a method of producing a plurality of hydrocarbon products, the method comprising:

introducing methane and a source of oxidant into an OCM reactor system capable of converting methane to ethylene at reactor inlet temperatures of between about 450° C. and 600° C. and reactor pressures of between about 15 psig and 125 psig, with C2+ selectivity of at least 50%, under conditions for the conversion of methane to ethylene;

recovering ethylene from the OCM reactor system; and introducing separate portions of the ethylene recovered from the OCM reactor system into at least two integrated, but discrete and different catalytic ethylene conversion reaction systems for converting ethylene into at least two different higher hydrocarbon products.

In another embodiment of the foregoing method, the at least two ethylene conversion systems are selected from selective and full range ethylene conversion systems. In some other embodiments, the at least two ethylene conversion systems comprise at least three ethylene conversion systems. For example, in some embodiments the at least two ethylene conversion systems comprise at least four ethylene conversion systems.

In yet more embodiments of the above method, the at least two ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In other aspects, the at least two ethylene conversion systems are selected from LAO systems that produce one or more of 1-butene, 1-hexene, 1-octene and 1-decene. For example, in some embodiments at least one of the at least two LAO processes comprises a selective LAO process, and in other exemplary embodiments at least one of the at least two ethylene conversion systems comprises a full range ethylene oligomerization system for producing higher hydrocarbons in the range of C4 to C30.

In other specific embodiments, the OCM reactor system comprises nanowire OCM catalyst material.

In different embodiments, the invention provides a method of producing a plurality of liquid hydrocarbon products, comprising:

converting methane to a product gas comprising ethylene using a catalytic reactor process; and contacting separate portions of the product gas with at least two discrete catalytic reaction systems selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In still different aspects of the disclosed invention, a method of producing a plurality of liquid hydrocarbon products is provided. The method comprises:

converting methane to ethylene using a catalytic reactor process;

recovering ethylene from the catalytic reactor process; and contacting separate portions of the ethylene recovered from the OCM reactor system with at least two discrete catalytic reaction systems selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

Other embodiments of the present disclosure are directed to a processing system for preparation of C+ hydrocarbon products from methane. For example, in some embodiments the invention provides a processing system comprising:

an OCM reactor system comprising an OCM catalyst, the OCM reactor system being fluidly connected at an input, to a source of methane and a source of oxidant;

an integrated ethylene conversion reactor system, the ethylene reactor system being configured to convert ethylene to a higher hydrocarbon; and a selective coupling between the OCM reactor system and the ethylene reactor system, the selective coupling configured to selectively direct a portion or all of the product gas to the ethylene conversion reactor system.

In variations of the above, the invention provides a processing system comprising:

an OCM reactor system comprising an OCM catalyst, the OCM reactor system being fluidly connected at an input, to a source of methane and a source of oxidant;

at least first and second catalytic ethylene conversion reactor systems, the first catalytic ethylene reactor system being configured to convert ethylene to a first higher hydrocarbon, and the second catalytic ethylene reactor system being configured to convert ethylene to a second higher hydrocarbon different from the first higher hydrocarbon; and a selective coupling between the OCM reactor system and the first and second catalytic ethylene reactor systems configured to selectively direct a portion or all of the product gas to each of the first and second catalytic ethylene reactor systems.

In some embodiments of the foregoing systems, the ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, ethylene copolymerization systems, and hydrocarbon polymer systems.

In still other embodiments of the foregoing systems, the OCM catalyst comprises a nanowire catalyst. In more embodiments, the system further comprises an ethylene recovery system fluidly coupled between the OCM reactor system and the at least first and second catalytic ethylene conversion reactor systems, the ethylene recovery system configured for enriching the product gas for ethylene.

In other different embodiments, the invention is directed to a processing system, the processing system comprising:

an OCM reactor system comprising an OCM catalyst, the OCM reactor system being fluidly connected at an input, to a source of methane and a source of oxidant;

an ethylene recovery system fluidly coupled to the OCM reactor system at an outlet, for recovering ethylene from an OCM product gas;

at least first and second catalytic ethylene conversion reactor systems, the first catalytic ethylene reactor system being configured to convert ethylene to a first higher hydrocarbon composition, and the second catalytic ethylene reactor system being configured to convert ethylene to a second higher hydrocarbon composition different from the first higher hydrocarbon composition; and a selective coupling between the outlet of the ethylene recovery system and the first and second catalytic ethylene reactor systems to selectively direct a portion or all of the ethylene recovered from the OCM product gas to each of the first and second catalytic ethylene reactor systems.

In some embodiments of the foregoing processing system, two or more of the at least two ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, ethylene copolymerization systems, and hydrocarbon polymer systems. In other embodiments, the OCM catalyst comprises a nanowire catalyst.

In still other embodiments, the catalyst systems used in any of the above described OCM reaction comprise nanowire catalysts. Such nanowire catalysts include substantially straight nanowires or nanowires having a curved, twisted or bent morphology. The actual lengths of the nanowire catalysts may vary. For example in some embodiments, the nanowires have an actual length of between 100 nm and 100 µm. In other embodiments, the nanowires have an actual length of between 100 nm and 10 µm. In other embodiments, the nanowires have an actual length of between 200 nm and 10 µm. In other embodiments, the nanowires have an actual length of between 500 nm and 5 µm. In other embodiments, the actual length is greater than 5 µm. In other embodiments, the nanowires have an actual length of between 800 nm and 1000 nm. In other further embodiments, the nanowires have an actual length of 900 nm. As noted below, the actual length of the nanowires may be determined by TEM, for example, in bright field mode at 5 keV.

The diameter of the nanowires may be different at different points along the nanowire backbone. However, the nanowires comprise a mode diameter (i.e., the most frequently occurring diameter). As used herein, the diameter of a nanowire refers to the mode diameter. In some embodiments, the nanowires have a diameter of between 1 nm and 10 µm, between 1 nm and 1 µm, between 1 nm and 500 nm, between 1 nm and 100 nm, between 7 nm and 100 nm, between 7 nm and 50 nm, between 7 nm and 25 nm, or between 7 nm and 15 nm. On other embodiments, the diameter is greater than 500 nm. As noted below, the diameter of the nanowires may be determined by TEM, for example, in bright field mode at 5 keV.

The nanowire catalysts may have different aspect ratios. In some embodiments, the nanowires have an aspect ratio of greater than 10:1. In other embodiments, the nanowires have an aspect ratio greater than 20:1. In other embodiments, the nanowires have an aspect ratio greater than 50:1. In other embodiments, the nanowires have an aspect ratio greater than 100:1.

In some embodiments, the nanowires comprise a solid core while in other embodiments, the nanowires comprise a hollow core. In general, the morphology of a nanowire (including length, diameter, and other parameters) can be determined by transmission electron microscopy (TEM). Transmission electron microscopy (TEM) is a technique whereby a beam of electrons is transmitted through an ultra thin specimen, interacting with the specimen as it passes through. An image is formed from the interaction of the electrons transmitted through the specimen. The image is magnified and focused onto an imaging device, such as a fluorescent screen, on a layer of photographic film or detected by a sensor such as a CCD camera. TEM techniques are well known to those of skill in the art.

In some embodiments, the nanowire catalysts comprise one or multiple crystal domains, e.g., monocrystalline or polycrystalline, respectively. In some other embodiments, the average crystal domain of the nanowires is less than 100 nm, less than 50 nm, less than 30 nm, less than 20 nm, less than 10 nm, less than 5 nm, or less than 2 nm. Crystal structure, composition, and phase, including the crystal domain size of the nanowires, can be determined by XRD.

Typically, the nanowire catalytic material comprises a plurality of nanowires. In certain embodiments, the plurality of nanowires form a mesh of randomly distributed and, to various degrees, interconnected nanowires, that presents a porous matrix.

The total surface area per gram of a nanowire or plurality of nanowires may have an effect on the catalytic performance. Pore size distribution may affect the nanowires catalytic performance as well. Surface area and pore size distribution of the nanowires or plurality of nanowires can be determined by BET (Brunauer, Emmett, Teller) measurements. BET techniques utilize nitrogen adsorption at various temperatures and partial pressures to determine the surface area and pore sizes of catalysts. BET techniques for determining surface area and pore size distribution are well known in the art. In some embodiments the nanowires have a surface area of between 0.0001 and 3000 $m^2/g$, between 0.0001 and 2000 $m^2/g$, between 0.0001 and 1000 $m^2/g$, between 0.0001 and 500 $m^2/g$, between 0.0001 and 100 $m^2/g$, between 0.0001 and 50 $m^2/g$, between 0.0001 and 20 $m^2/g$, between 0.0001 and 10 $m^2/g$ or between 0.0001 and 5 $m^2/g$. In some embodiments the nanowires have a surface area of between 0.001 and 3000 $m^2/g$, between 0.001 and 2000 $m^2/g$, between 0.001 and 1000 $m^2/g$, between 0.001 and 500 $m^2/g$, between 0.001 and 100 $m^2/g$, between 0.001 and 50 $m^2/g$, between 0.001 and 20 $m^2/g$, between 0.001 and 10 $m^2/g$ or between 0.001 and 5 $m^2/g$. In some other embodiments the nanowires have a surface area of between 2000 and 3000 $m^2/g$, between 1000 and 2000 $m^2/g$, between 500 and 1000 $m^2/g$, between 100 and 500 $m^2/g$, between 10 and 100 $m^2/g$, between 5 and 50 $m^2/g$, between 2 and 20 $m^2/g$ or between 0.0001 and 10 $m^2/g$. In other embodiments, the nanowires have a surface area of greater than 2000 $m^2/g$, greater than 1000 $m^2/g$, greater than 500 $m^2/g$, greater than 100 $m^2/g$, greater than 50 $m^2/g$, greater than 20 $m^2/g$, greater than 10 $m^2/g$, greater than 5 $m^2/g$, greater than 1 $m^2/g$, greater than 0.0001 $m^2/g$.

The nanowire catalysts and catalyst compositions used in conjunction with the processes and systems of some embodiments of the invention may have any number of compositions and/or morphologies. These nanowire catalysts may be inorganic and either polycrystalline or monocrystalline. In some other embodiments, the nanowires are inorganic and polycrystalline. In certain examples, the nanowire catalysts comprise one or more elements from any of Groups 1 through 7, lanthanides, actinides or combinations thereof. Thus in certain aspects, the catalysts comprise an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof.

In still other cases, the nanowire catalysts comprise one or more metal elements from any of Groups 1-7, lanthanides, actinides or combinations thereof, for example, the nanowires may be mono-metallic, bi-metallic, tri-metallic, etc. (i.e., contain one, two, three, etc. metal elements), where the metal elements may be present in the nanowires in elemental or oxidized form, or in the form of a compound comprising a metal element. The metal element or compound comprising the metal element may be in the form of oxides, hydroxides, oxyhydroxides, salts, hydrated oxides, carbonates, oxy-carbonates, sulfates, phosphates, acetates, oxalates and the like. The metal element or compound comprising the metal element may also be in the form of any of a number of different polymorphs or crystal structures.

In certain examples, metal oxides may be hygroscopic and may change forms once exposed to air, may absorb carbon dioxide, may be subjected to incomplete calcination or any combination thereof. Accordingly, although the nanowires are often referred to as metal oxides, in certain embodiments the nanowires also comprise hydrated oxides, oxyhydroxides, hydroxides, oxycarbonates (or oxide carbonates), carbonates or combinations thereof.

In many cases, the nanowires comprise one or more metal elements from Group 1, Group 2, Group 3, Group 4, Group 5, Group 6, Group 7, lanthanides, and/or actinides, or combinations of these, as well as oxides of these metals. In other cases, the nanowires comprise hydroxides, sulfates, carbonates, oxide carbonates, acetates, oxalates, phosphates (including hydrogen phosphates and dihydrogenphosphates), oxy-carbonates, oxyhalides, hydroxyhalides, oxyhydroxides, oxysulfates, mixed oxides or combinations thereof of one or more metal elements from any of Groups 1-7, lanthanides, actinides or combinations thereof. Examples of such nanowire materials include, but are not limited to nanowires comprising, e.g., $Li_2CO_3$, $LiOH$, $Li_2O$, $Li_2C_2O_4$, $Li_2SO_4$, $Na_2CO_3$, $NaOH$, $Na_2O$, $Na_2C_2O_4$, $Na_2SO_4$, $K_2CO_3$, $KOH$, $K_2O$, $K_2C_2O_4$, $K_2SO_4$, $Cs_2CO_3$, $CsOH$, $Cs_2O$, $CsC_2O_4$, $CsSO_4$, $Be(OH)_2$, $BeCO_3$, $BeO$, $BeC_2O_4$. $BeSO_4$, $Mg(OH)_2$, $MgCO_3$, $MgO$, $MgC_2O_4$. $MgSO_4$, $Ca(OH)_2$, $CaO$, $CaCO_3$, $CaC_2O_4$, $CaSO_4$, $Y_2O_3$, $Y_2(CO_3)_3$, $Y(OH)_3$, $Y_2(C_2O4)_3$, $Y_2(SO_4)_3$, $Zr(OH)_4$, $ZrO(OH)_2$, $ZrO2$, $Zr(C_2O_4)_2$, $Zr(SO_4)_2$, $Ti(OH)_4$, $TiO(OH)_2$, $TiO_2$, $Ti(C_2O_4)_2$, $Ti(SO_4)_2$, $BaO$, $Ba(OH)_2$, $BaCO_3$, $BaC_2O_4$, $BaSO_4$, $La(OH)_3$, $La_2O_3$, $La_2(C_2O_4)_3$, $La_2(SO_4)_3$, $La_2(CO_3)_3$, $Ce(OH)_4$, $CeO_2$, $Ce_2O_3$, $Ce(C_2O_4)_2$, $Ce(SO_4)_2$, $Ce(CO_3)_2$, $ThO_2$, $Th(OH)_4$, $Th(C_2O_4)_2$, $Th(SO_4)_2$, $Th(CO_3)_2$, $Sr(OH)_2$, $SrCO_3$, $SrO$, $SrC_2O_4$, $SrSO_4$, $Sm_2O_3$, $Sm(OH)_3$, $Sm_2(CO_3)_3$, $Sm_2(C_2O_4)_3$, $Sm_2(SO_4)_3$, $LiCa_2Bi_3O_4Cl_6$, $NaMnO_4$, $Na_2WO_4$, $NaMn/WO_4$, $CoWO_4$, $CuWO_4$, $K/SrCoO_3$, $K/Na/SrCoO_3$, $Na/SrCoO_3$, $Li/SrCoO_3$, SrCoO$_3$, Mg$_6$MnO$_8$, LiMn$_2$O$_4$, Li/Mg$_6$MnO$_8$, Na$_{10}$Mn/W$_5$O$_{17}$, Mg$_3$Mn$_3$B$_2$O$_{10}$, Mg$_3$(BO$_3$)$_2$, molybdenum oxides, molybdenum hydroxides, molybdenum oxalates, molybdenum sulfates, Mn$_2$O$_3$, Mn$_3$O$_4$, manganese oxides, manganese hydroxides, manganese oxalates, manganese sulfates, manganese tungstates, manganese carbonates, vanadium oxides, vanadium hydroxides, vanadium oxalates, vanadium sulfates, tungsten oxides, tungsten hydroxides, tungsten oxalates, tungsten sulfates, neodymium oxides, neodymium hydroxides, neodymium carbonates, neodymium oxalates, neodymium sulfates, europium oxides, europium hydroxides, europium carbonates, europium oxalates, europium sulfates, praseodymium oxides, praseodymium hydroxides, praseodymium carbonates, praseodymium oxalates, praseodymium sulfates, rhenium oxides, rhenium hydroxides, rhenium oxalates, rhenium sulfates, chromium oxides, chromium hydroxides, chromium oxalates, chromium sulfates, potassium molybdenum oxides/silicon oxide or combinations thereof.

Still other examples of these nanowire materials include, but are not limited to, nanowires comprising, e.g., Li$_2$O, Na$_2$O, K$_2$O, Cs$_2$O, BeO MgO, CaO, ZrO(OH)$_2$, ZrO$_2$, TiO$_2$, TiO(OH)$_2$, BaO, Y$_2$O$_3$, La$_2$O$_3$, CeO$_2$, Ce$_2$O3, ThO$_2$, SrO, Sm$_2$O$_3$, Nd$_2$O$_3$, Eu$_2$O$_3$, Pr$_2$O$_3$, LiCa$_2$Bi$_3$O$_4$C$_{16}$, NaMnO$_4$, Na$_2$WO$_4$, Na/Mn/WO$_4$, Na/MnWO$_4$, Mn/WO$_4$, K/SrCoO$_3$, K/Na/SrCoO$_3$, K/SrCoO$_3$, Na/SrCoO$_3$, Li/SrCoO$_3$, SrCoO$_3$, Mg$_6$MnO$_8$, Na/B/Mg$_6$MnO$_8$, Li/B/Mg$_6$MnO$_8$, Zr$_2$Mo$_2$O$_8$, molybdenum oxides, Mn$_2$O$_3$, Mn$_3$O$_4$, manganese oxides, vanadium oxides, tungsten oxides, neodymium oxides, rhenium oxides, chromium oxides, or combinations thereof. A variety of different nanowire compositions have been described in, e.g., Published U.S. Patent Application No. 2012-0041246 and U.S. patent application Ser. No. 13/689,611, filed Nov. 29, 2012 (the full disclosures of which are incorporated herein in their entirety for all purposes), and are envisioned for use in conjunction with the present invention.

Products produced from these catalytic reactions typically include CO, CO$_2$, H$_2$0, C2+ hydrocarbons, such as ethylene, ethane, and larger alkanes and alkenes, such as propane and propylene. In some embodiments, the OCM reactor systems operate to convert methane into desired higher hydrocarbon products (ethane, ethylene, propane, propylene, butanes, pentanes, etc.), collectively referred to as C2+ compounds, with high yield. In particular, the progress of the OCM reaction is generally discussed in terms of methane conversion, C2+ selectivity, and C2+ yield. As used herein, methane conversion generally refers to the percentage or fraction of methane introduced into the reaction that is converted to a product other than methane. C2+ selectivity generally refers to the percentage of all non-methane, carbon containing products of the OCM reaction that are the desired C2+ products, e.g., ethane, ethylene, propane, propylene, etc. Although primarily stated as C2+ selectivity, it will be appreciated that selectivity may be stated in terms of any of the desired products, e.g., just C2, or just C2 and C3. Finally, C2+ yield generally refers to the amount of carbon that is incorporated into a C2+ product as a percentage of the amount of carbon introduced into a reactor in the form of methane. This may generally be calculated as the product of the conversion and the selectivity divided by the number of carbon atoms in the desired product. C2+ yield is typically additive of the yield of the different C2+ components included in the C2+ components identified, e.g., ethane yield+ethylene yield+propane yield+propylene yield etc.).

Exemplary OCM processes and systems typically provide a methane conversion of at least 10% per process pass in a single integrated reactor system (e.g., single isothermal reactor system or integrated multistage adiabatic reactor system), with a C2+ selectivity of at least 50%, but at reactor inlet temperatures of between 400 and 600° C. and at reactor inlet pressures of between about 15 psig and about 150 psig. Thus, the catalysts employed within these reactor systems are capable of providing the described conversion and selectivity under the described reactor conditions of temperature and pressure. In the context of some OCM catalysts and system embodiments, it will be appreciated that the reactor inlet or feed temperatures typically substantially correspond to the minimum "light-off" or reaction initiation temperature for the catalyst or system. Restated, the feed gases are contacted with the catalyst at a temperature at which the OCM reaction is able to be initiated upon introduction to the reactor. Because the OCM reaction is exothermic, once light-off is achieved, the heat of the reaction would be expected to maintain the reaction at suitable catalytic temperatures, and even generate excess heat.

In certain aspects, the OCM reactors and reactor systems, when carrying out the OCM reaction, operate at pressures of between about 15 psig and about 125 psig at the above described temperatures, while providing the conversion and selectivity described above, and in even more embodiments, at pressures less than 100 psig, e.g., between about 15 psig and about 100 psig.

Examples of particularly useful catalyst materials are described in, for example, Published U.S. Patent Application No. 2012-0041246, as well as patent application Ser. No. 13/479,767, filed May 24, 2012, and Ser. No. 13/689,611, filed Nov. 29, 2012, previously incorporated herein by reference in their entirety for all purposes. In some embodiments, the catalysts comprise bulk catalyst materials, e.g., having relatively undefined morphology or, in certain embodiments, the catalyst material comprises, at least in part, nanowire containing catalytic materials. In either form, the catalysts used in accordance with the present invention may be employed under the full range of reaction conditions described above, or in any narrower described range of conditions. Similarly, the catalyst materials may be provided in a range of different larger scale forms and formulations, e.g., as mixtures of materials having different catalytic activities, mixtures of catalysts and relatively inert or diluent materials, incorporated into extrudates, pellets, or monolithic forms, or the like. Ranges of exemplary catalyst forms and formulations are described in, for example, U.S. patent application Ser. No. 13/901,319 and 61/909,840, the full disclosures of which are incorporated herein by reference in their entireties for all purposes.

The reactor vessels used for carrying out the OCM reaction in the OCM reactor systems of the invention may include one or more discrete reactor vessels each containing OCM catalyst material, fluidly coupled to a methane source and a source of oxidant as further discussed elsewhere herein. Feed gas containing methane (e.g., natural gas) is contacted with the catalyst material under conditions suitable for initiation and progression of the reaction within the reactor to catalyze the conversion of methane to ethylene and other products.

For example, in some embodiments the OCM reactor system comprises one or more staged reactor vessels operating under isothermal or adiabatic conditions, for carrying out OCM reactions. For adiabatic reactor systems, the reactor systems may include one, two, three, four, five or more staged reactor vessels arranged in series, which are fluidly connected such that the effluent or "product gas" of one reactor is directed, at least in part, to the inlet of a subsequent reactor. Such staged serial reactors provide higher yield for the overall process, by allowing catalytic conversion of previously unreacted methane. These adiabatic reactors are generally characterized by the lack of an integrated thermal control system used to maintain little or no temperature gradient across the reactor. With no integrated temperature control system, the exothermic nature of the OCM reaction results in a temperature gradient across the reactor indicative of the progress of the reaction, where the inlet temperature can range from about 450° C. to about 600° C., while the outlet temperature ranges from about 700° C. to about 900° C. Typically, such temperature gradients can range from about 100° C. to about 450° C. By staging adiabatic reactors, with interstage cooling systems, one can step through a more complete catalytic reaction without generating extreme temperatures, e.g., in excess of 900° C.

In operation of certain embodiments, methane-containing feed gas is introduced into the inlet side of a reactor vessel, e.g., the first reactor in a staged reactor system. Within this reactor, the methane is converted into C2+ hydrocarbons, as well as other products, as discussed above. At least a portion of the product gas stream is then cooled to an appropriate temperature and introduced into a subsequent reactor stage for continuation of the catalytic reaction. In particular, the effluent from a preceding reactor, which in some cases may include unreacted methane, can provide at least a portion of the methane source for a subsequent reactor. An oxidant source and a methane source, separate from the unreacted methane from the first reactor stage, are also typically coupled to the inlet of each subsequent reactor.

In alternative aspects, the reactor systems include one or more 'isothermal' reactors, that maintain a relatively low temperature gradient across the overall reactor bed, e.g., between the inlet gas and outlet or product gas, through the inclusion of integrated temperature control elements, such as coolant systems that contact heat exchange surfaces on the reactor to remove excess heat, and maintain a flat or insignificant temperature gradient between the inlet and outlet of the reactor. Typically, such reactors utilize molten salt or other coolant systems that operate at temperatures below 593° C. As with adiabatic systems, isothermal reactor systems may include one, two, three or more reactors that may be configured in serial or parallel orientation. Reactor systems for carrying out these catalytic reactions are also described in U.S. patent application Ser. No. 13/900,898, the full disclosure of which is incorporated herein by reference in its entirety for all purposes.

The OCM reactor systems used in certain embodiments of the present invention also typically include thermal control systems that are configured to maintain a desired thermal or temperature profile across the overall reactor system, or individual reactor vessels. In the context of adiabatic reactor systems, it will be appreciated that the thermal control systems include, for example, heat exchangers disposed upstream, downstream or between serial reactors within the overall system in order to maintain the desired temperature profile across the one or more reactors. In the context of reactors carrying out exothermic reactions, like OCM, such thermal control systems also optionally include control systems for modulating flow of reactants, e.g., methane containing feed gases and oxidant, into the reactor vessels in response to temperature information feedback, in order to modulate the reactions to achieve the thermal profiles of the reactors within the desired temperature ranges. These systems are also described in co-pending U.S. patent application Ser. No. 13/900,898, previously incorporated herein by reference.

For isothermal reactors, such thermal control systems include the foregoing, as well as integrated heat exchange components, such as integrated heat exchangers built into the reactors, such as tube/shell reactor/heat exchangers, where a void space is provided surrounding a reactor vessel or through which one or more reactor vessels or tubes pass. A heat exchange medium is then passed through the void to remove heat from the individual reactor tubes. The heat exchange medium is then routed to an external heat exchanger to cool the medium prior to recirculation into the reactor.

Following the OCM process, ethylene optionally may be recovered from the OCM product gas using an ethylene recovery process that separates ethylene present in the product gas from other components, such as residual, i.e., unreacted methane, ethane, and higher hydrocarbons, such as propanes, butanes, pentanes and the like. Alternatively, the OCM product gas is used in subsequent reactions, as described below, without further purification or separation of the ethylene. In various other embodiments, the OCM product gas is enriched for ethylene before being used in subsequent reactions. In this respect, "enriched" includes, but is not limited to, operations which increases the overall mol % of ethylene in the product gas.

In accordance with the present invention, ethylene derived from methane, e.g., using the above-described OCM processes and systems, is further processed into higher hydrocarbon compositions, and particularly liquid hydrocarbon compositions. For ease of discussion, reference to OCM processes and systems, when referring to their inclusion in an overall process flow, from methane to higher hydrocarbon compositions, also optionally includes intermediate process steps involved in purification of ethylene from an OCM product gas, e.g., recycling of product gases through the OCM reactor system, separations of methane and higher hydrocarbons, e.g., NGLs and other C2+ compounds, from the OCM product gas, and the like. Examples of such intermediate processes include, for example, cryogenic or lean oil separation systems, temperature swing adsorption (TSA), pressure swing adsorption (PSA), and membrane separations, for separation of different hydrocarbon and other components from ethylene, e.g., CO, $CO_2$, water, nitrogen, residual methane, ethane, propane, and other higher hydrocarbon compounds, potentially present in the OCM product gas. Examples of such systems are described in, e.g., U.S. patent application Ser. Nos. 13/739,954, 61/773,669 and 61/669,523, the full disclosures of which are incorporated herein by reference in their entirety for all purposes.

Figure 2:
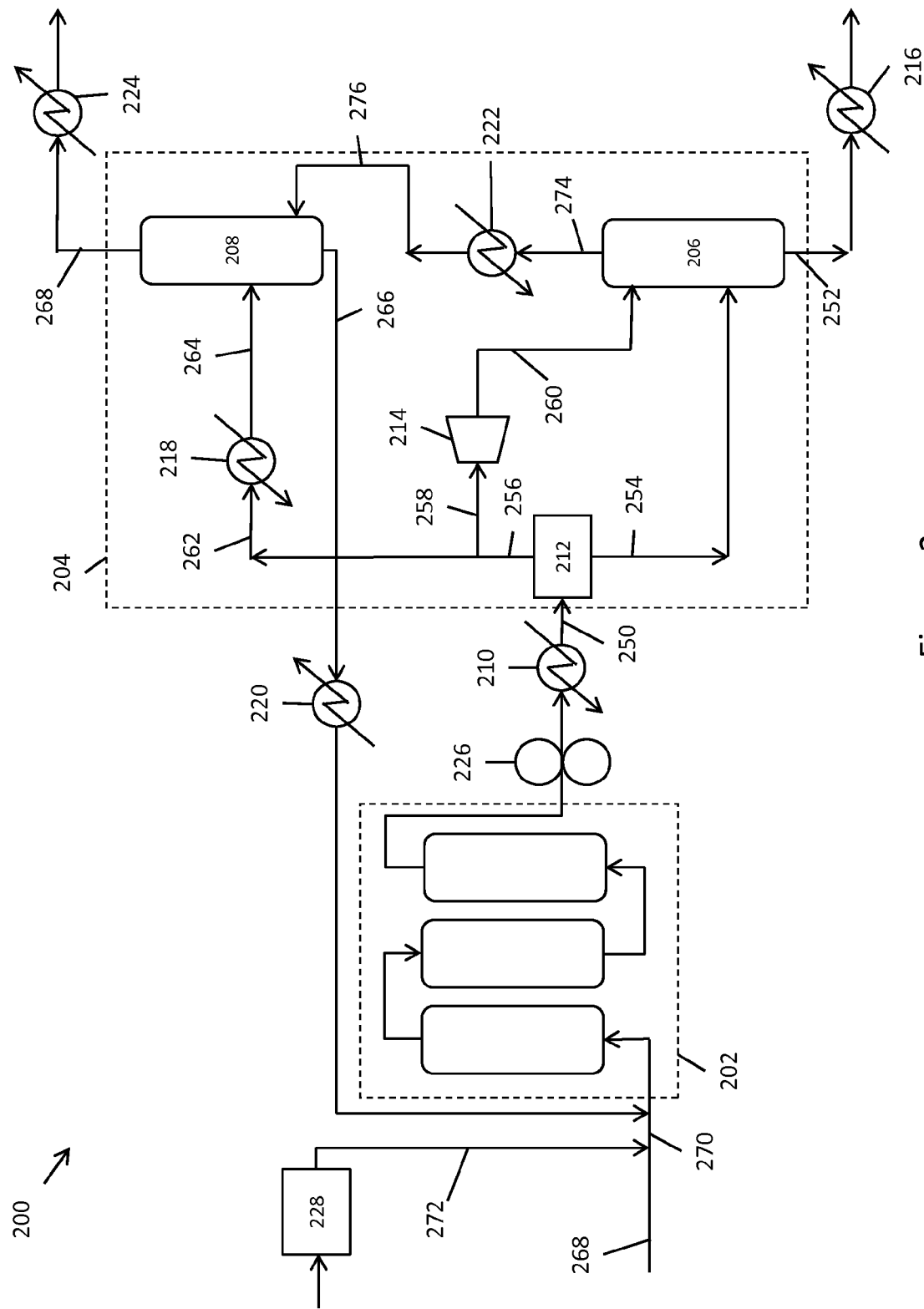
FIG. 2 schematically illustrates an integrated OCM system with integrated separations system.

FIG. 2 schematically illustrates an exemplary OCM system with integrated separations system component or components. In particular, shown in FIG. 2 is an exemplary process flow diagram depicting a process 200 for methane based C2 production, in a product gas from an OCM reactor or reactors 202, and separation process 204, that includes a first separator 206 providing the C2-rich effluent 252 and a methane/nitrogen-rich effluent 274. In the embodiment illustrated in FIG. 2, the OCM product gas from the OCM reactor(s) 202 is compressed through compressor 226. The temperature of the compressed OCM product gas 250 is reduced using one or more heat exchangers 210. The temperature of the compressed OCM product gas 250 may be reduced through the use of an external provided cooling media, introduction of or thermal exchange with a cool process stream, or combinations of these. Reducing the temperature of the OCM product gas 250 will typically condense at least a portion of the higher boiling point components in the compressed OCM product gas 250, including at least a portion of the C2 and heavier hydrocarbon components present in the compressed OCM product gas 250.

At least a portion of the condensed high boiling point components can be separated from the compressed OCM product gas 250 using one or more liquid gas separators, such as knockout drums 212 to provide an OCM product gas condensate 254 and a compressed OCM product gas 256. The OCM product gas condensate 254 is introduced to the first separator 206 and at least a portion 258 of the compressed OCM product gas 256 can be introduced to one or more turboexpanders 214. The isentropic expansion of the compressed OCM product gas 258 within the turboexpanders 214 can produce shaft work useful for driving one or more compressors or other devices in the separation unit 204. The isentropic expansion of the compressed OCM product gas 258 with the turboexpanders reduces the temperature of the compressed OCM product gas 260 that exits from the one or more turboexpanders. The compressed OCM product gas 260 from the one or more turboexpanders 214 is introduced to the first separator 206.

The first separator 206 can be any system, device or combination of systems and devices suitable for promoting the separation of C2 and heavier hydrocarbons from a gas stream that includes methane and nitrogen. For example, cryogenic distillation at a relatively high temperature may be used to promote separation of the C2 and heavier hydrocarbons from the methane and nitrogen components in the gas stream. The C2-rich effluent 252 is withdrawn from the first separator 206 and a mixed nitrogen and methane containing gas mixture 274 is also withdrawn from the first separator 254. The nitrogen content of the nitrogen/methane containing gas mixture 274 withdrawn from the first separator 206 can be about 95 mol % or less; about 85 mol % or less; about 75 mol % or less; about 55 mol % or less; about 30 mol % or less. The balance of the nitrogen/methane gas mixture 254 comprises principally methane with small quantities of hydrogen, carbon monoxide, and inert gases such as argon. The nitrogen/methane rich gas 274 is then further cooled using heat exchanger(s) 222, and the cooled nitrogen/methane containing gas 276 is then introduced into second separator 208, described in more detail, below.

In at least some embodiments, the first separator functions as a "demethanizer" based upon its ability to separate methane from the C2 and heavier hydrocarbon components. An exemplary first separator 206 includes a vertical distillation column operating at below ambient temperature and above ambient pressure. In particular, the operating temperature and pressure within the first separator 206 can be established to improve the recovery of the desired C2 hydrocarbons in the C2-rich effluent 252. In exemplary embodiments, the first separator 206 can have an overhead operating temperature of from about −260° F. (−162° C.) to about −180° F. (−118° C.); about −250° F. (−157° C.) to about −190° F. (−123° C.); about −240° F. (−151° C.) to about −200° F. (−129° C.; or even from about −235° F. (−148° C.) to about −210° F. (−134° C.) and a bottom operating temperature of from about −150° F. (−101° C.) to about −50° F. (−46° C.); about −135° F. (−93° C.) to about −60° F. (−51° C.); from about −115° F. (−82° C.) to about −70° F. (−57° C.); or about −100° F. (−73° C.) to about −80° F. (−62° C.). In an exemplary aspect, the first separator 206 may operate at pressures of from about 30 psig (205 kPa) to about 130 psig (900 kPa); about 40 psig (275 kPa) to about 115 psig (790 kPa); about 50 psig (345 kPa) to about 95 psig (655 kPa); or about 60 psig (415 kPa) to about 80 psig (550 kPa).

The temperature of at least a portion of the C2-rich effluent 252 from the first separator 206 can be increased in one or more heat exchangers 216, again using an externally supplied heat transfer medium, introduction of, or thermal contact, with a warmer process flow stream, or a combination of these, or other heating systems. The one or more heat exchanger devices 216 may include any type of heat exchange device or system, including but not limited to one or more plate and frame, shell and tube or similar heat exchanger system. After exiting the one or more heat exchangers 216, the heated C2-rich effluent 252 may be at temperatures of 50° F. (10° C.) or less; 25° F. (−4° C.) or less; about 0° F. (−18° C.) or less; about −25° F. (−32° C.) or less; or about −50° F. (−46° C.) or less. Furthermore, the pressure may be about 130 psig (900 kPa) or less; about 115 psig (790 kPa or less; about 100 psig (690 kPa) or less; or about 80 psig (550 kPa) or less.

In some embodiments, a portion 262 of the OCM product gas 256 removed from the knockout drum 212 and not introduced into the one or more turboexpanders 214 can be cooled using one or more heat exchangers 218. As noted previously, the heat exchangers may include any type of heat exchanger suitable for the operation. The temperature of the portion 262 of the OCM product gas 256 can be decreased using one or more refrigerants, one or more relatively cool process flows, or combinations of these. The cooled portion 264 of the OCM product gas 256 containing a mixture of nitrogen and methane is introduced into the second separator 208.

The second separator 208 may include any system, device or combination of systems and devices suitable for separating methane from nitrogen. For example, cryogenic distillation at a relatively low temperature can be used to promote the separation of liquid methane from gaseous nitrogen within the second separator 208. An exemplary second separator 208 may include another vertical distillation column operating significantly below ambient temperature and above ambient pressure, and also generally below the temperature of a cryogenic distillation column operating as the first separator, e.g., as described above. For example, the second separator 208 may have an overhead operating temperature of from about −340° F. (−210° C.) to about −240° F. (−151° C.); from about −330° F. (−201° C.) to about −250° F. (−157° C.); about −320° F. (−196° C.) to about −260° F. (−162° C.); about −310° F. (−190° C.) to about −270° F. (−168° C.); or about 300° F. (−184° C.) to about −280° F. (−173° C.); and a bottom operating temperature of from about −280° F. (−173° C.) to about −170° F. (112° C.); about −270° F. (−168° C.) to about −180° F. (−118° C.); about −260° F. (−162° C.) to about −190° F. (−123° C.); about −250° F. (−159° C.) to about −200° F. (−129° C.); or about −240° F. (−151° C. to about −210° F. (−134° C.). In exemplary embodiments, the second separator 208 will typically operate at pressures of from about 85 psig (585 kPa) or less; about 70 psig (480 kPa) or less; about 55 psig (380 kPa) or less; or about 40 psig (275 kPa) or less.

The temperature of at least a portion of the methane-rich effluent 266 from the second separator 208 can be increased using one or more heat exchangers 220, as described above. After exiting the one or more heat exchangers 220, in exemplary embodiments the temperature of the methane-rich effluent 266 may be about 125° F. (52° C.) or less; about 100° F. (38° C.) or less; or about 90° F. (32° C.) or less, while the pressure of the effluent 266 may be about 150 psig (1035 kPa) or less; about 100 psig (690 kPa) or less, or about 50 psig (345 kPa) or less. In an embodiment, e.g., schematically illustrated in FIG. 2, at least a portion of the methane-rich effluent 266 may be recycled back into the feedstock gas 268 for the OCM reactor(s) 202, the feedstock gas/oxygen mixture 270 the compressed oxygen containing gas 272 (from compressor 228) or directly to the one or more OCM reactors 202.

The temperature of at least a portion of the nitrogen-rich effluent 268 from second separator 208 can be increased using one or more heat exchangers 224 like those described above, such that the temperature may be raised to about 125° F. (52° C.) or less; 100° F. (38° C.) or less; or about 90° F. (32° C.) or less, with a pressure of about 150 psig (1035 kPa) or less; about 100 psig (690 kPa) or less; or about 50 psig (345 kPa) or less.

As will be appreciated, in integrating overall systems, while the one or more heat exchangers 210, 216, 218, 220, 222 and 224 are illustrated as separate heat exchange devices, such heat exchangers may be integrated into one or more integrated systems, where the different temperature process flows may be provided in thermal contact, e.g., as heat exchange media for each other, with in the heat exchange device or system. In particular, a cooled process flow that is desired to be heated may be passed through an opposing portion of a heat exchanger from a heated process flow that is desired to be cooled, such that the heat from the heated flow heats the cooler flow, and is, as a result, itself cooled.

Ethylene products of these processes, e.g., in C2-rich effluent 252, are then subjected to additional processing to yield the desired higher hydrocarbon compositions. For ease of discussion, the processes and systems for converting ethylene into higher hydrocarbons are referred to generally as ethylene conversion processes and systems. A number of exemplary processes for ethylene conversion are described in greater detail below.

III. Integrated and Selectable Ethylene Conversion

As noted previously, in the context of certain aspects of the invention, the conversion of methane to ethylene, as well as the conversion of ethylene to higher hydrocarbon compositions, is carried out in integrated processes. As used herein, integrated processes refer to two or more processes or systems that are fluidly integrated or coupled together. Thus, within this aspect of the invention, the process for conversion of methane to ethylene is fluidly connected to one or more processes for ethylene conversion to one or more higher hydrocarbon compounds. Fluid integration or fluid coupling generally refers to a persistent fluid connection or fluid coupling between two systems within an overall system or facility. Such persistent fluid communication typically refers to an interconnected pipeline network coupling one system to another. Such interconnected pipelines may also include additional elements between two systems, such as control elements, e.g., heat exchangers, pumps, valves, compressors, turbo-expanders, sensors, as well as other fluid or gas transport and/or storage systems, e.g., piping, manifolds, storage vessels, and the like, but are generally entirely closed systems, as distinguished from two systems where materials are conveyed from one to another through any non-integrated component, e.g., railcar or truck transport, or systems that are not co-located in the same facility or immediately adjacent facilities. As used herein, fluid connection and/or fluid coupling includes complete fluid coupling, e.g., where all effluent from a given point such as an outlet of a reactor, is directed to the inlet of another unit with which the reactor is fluidly connected. Also included within such fluid connections or couplings are partial connections, e.g., where only a portion of the effluent from a given first unit is routed to a fluidly connected second unit. Further, although stated in terms of fluid connections, it will be appreciated that such connections include connections for conveying either or both of liquids and/or gas.

In accordance with certain aspects of the invention, a methane to ethylene conversion process is not just integrated with a single ethylene conversion process, but instead, is integrated with multiple (i.e., two or more) different ethylene conversion processes or systems. In particular, ethylene produced from a single methane feed stream may be converted to multiple different products using multiple different ethylene conversion processes. For example, in some embodiments a single OCM reactor system is fluidly connected to one, two, three, four, five or more different catalytic or other reactor systems for further conversion of the ethylene containing product of the OCM reactor system (also referred to herein as the "ethylene product") to multiple different higher hydrocarbon compositions.

In certain aspects, the ethylene product is selectively directed in whole or in part to any one or more of the various ethylene conversion processes or systems integrated with the OCM reactor system. For example, at any given time all of the ethylene product produced through an OCM reactor system may be routed through a single process. Alternatively, a portion of the ethylene product may be routed through a first ethylene conversion process or system, while some or all of the remaining ethylene product is routed through one, two, three, four or more different ethylene conversion systems.

Although described in terms of directing ethylene streams to a single or multiple different ethylene conversion processes, in certain preferred aspects, those ethylene streams may be relatively dilute ethylene streams, e.g., that contain other components in addition to ethylene, such as other products of the OCM reaction, unreacted feed gases, or other by products. Typically, such other components may include additional reaction products, unreacted feedgases, or other reactor effluents from an ethylene production process, e.g., OCM, such as methane, ethane, propane, propylene, CO, $CO_2$, $O_2$, $N_2$, $H_2$, and/or water. The use of dilute ethylene streams, and particularly those containing other hydrocarbon components is particularly advantageous in the ethylene conversion processes used in conjunction with the invention. In particular, because these ethylene conversion processes utilize more dilute and less pure streams, the incoming ethylene streams are not required to go through as stringent a separations process or processes as would typically be required for other processes intended to produce higher purity ethylene, e.g., cryogenic separations systems, lean oil separators, TSA and PSA based separations processes. These separations processes typically have relatively high capital costs that scale, at least in part, based upon the volume of incoming gases. As such, separation processes for highly dilute ethylene streams can have substantially high capital and operating costs associated with them. By providing less stringent separations requirements on these ethylene streams, one can substantially reduce the capital costs. Further, because the ethylene conversion processes used in conjunction with the invention typically result in the production of desired liquid hydrocarbons, subsequent separation of gas co-products, or unreacted feed gases is made much simpler.

In addition to reducing capital and operating costs, the use of ethylene streams that comprise additional hydrocarbon components can enhance the product slate emanating from the ethylene conversion processes through which those ethylene streams are routed. In particular, the presence of higher order hydrocarbons, C3, C4, C5, etc. in the ethylene streams entering into the ethylene conversion processes can improve the overall efficiency of those processes, by providing enriched starting materials, and also affects the overall carbon efficiency of the OCM and ethylene conversion processes, by ensuring that a greater fraction of the carbon input is converted to higher hydrocarbon products.

While ethylene streams being routed to the ethylene conversion processes of the invention may range anywhere from trace concentrations of ethylene to pure or substantially pure ethylene, e.g., approaching 100% ethylene, the dilute ethylene streams described herein may generally be characterized as having anywhere from about 1% to about 50% ethylene, preferably, between about 5% and about 25% ethylene, and in further preferred aspects, between about 10% and about 25% ethylene, in addition to other components. In other embodiments, the ethylene feed gas comprises less than about 5% ethylene, for example less than about 4%, less than about 3%, less than about 2% or even less than about 1% ethylene. In some embodiments, the dilute ethylene product gases employed in the ethylene conversion processes further comprise one or more gases which are either produced during the OCM reaction or are unreacted during the OCM process. For example, in some embodiments the product gas comprises ethylene at any of the foregoing concentrations and one or more gas selected from $CO_2$, CO, $H_2$, $H_2O$, $C_2H_6$, $CH_4$ and C3+ hydrocarbons. In certain embodiments, such dilute ethylene feed gasses, which optionally include one or more of the foregoing gases are advantageous for use in reactions comprising conversion of ethylene to higher olefins and/or saturated hydrocarbons, for example conversion of ethylene to liquid fuels such as gasoline diesel or jet fuel at higher efficiencies (e.g., from methane) than previously attainable.

By utilizing dilute ethylene streams to feed into one or more ethylene conversion processes, one eliminates the need to separate or purify the ethylene coming into the process, e.g., as a product of an OCM reaction process. The elimination of additional costly process steps is particularly useful where the ethylene conversion processes are used to produce lower margin products, such as gasoline, diesel or jet fuel or blendstocks for these fuels. In particular, where the desired product is a lower value product, one may pass the OCM feed gases directly into one or more ethylene conversion processes that produce hydrocarbon mixtures that can be used as gasoline, diesel fuel or jet fuel or their blendstocks. Such direct passage may be in the absence of any intermediate purification steps, such as any processes used for the removal of the above described impurities. Alternatively, it may include certain purification steps to separate out some or all of the non-hydrocarbon impurities, e.g., $N_2$, $CO_2$, CO, $H_2$, etc. The direct passage may avoid any hydrocarbon fractionation, including removal of any of C1, C2, C3, C4 compounds, etc., or it may include some fractionation, e.g., to enhance carbon efficiency. For example, such included fractionation may include separation of methane and or ethane from the OCM effluent gas to recycle back to the OCM process. In addition to the foregoing, the presence of additional components such as $CO_2$, $H_2O$ and $H_2$ in the feed streams would also be expected to improve catalyst lifetime in the ethylene conversion processes by reducing deactivation, thereby requiring fewer catalyst regeneration cycles.

In contrast, where one desires to produce more selectively pure compounds, e.g., aromatic compounds, one will often need to pretreat the feed gases to remove many of the non-ethylene impurities.

Other components of these dilute ethylene streams may include co-products of the ethylene production processes, e.g., OCM reactions, such as other C2+ hydrocarbons, like ethane, propane, propylene, butane, pentane, and larger hydrocarbons, as well as other products such as CO, $CO_2$, $H_2$, $H_2O$, $N_2$, and the like.

A variety of different ethylene conversion processes may be employed in the various aspects of the present invention to produce higher hydrocarbon materials for use in, e.g., chemical manufacturing, polymer production, fuel production, as well as a variety of other products. In particular, the ethylene produced using the OCM processes may be oligomerized and/or reacted by a variety of different processes and reactor systems for producing linear alpha-olefins (LAOs), olefinic linear and/or olefinic branched hydrocarbons, saturated linear and/or branched hydrocarbons, saturated and/or olefinic cyclic hydrocarbons, aromatic hydrocarbons, oxygenated hydrocarbons, halogenated hydrocarbons, alkylated aromatics, and/or hydrocarbon polymers.

A. Olefinic Products and Processes

As noted above, the ethylene conversion processes employed in the integrated processes and systems of the invention may produce olefinic products for use in a variety of different end products or applications. For example, a portion or all of the ethylene produced by the OCM process may be routed through one or more catalytic processes or systems to oligomerize ethylene into LAOs of ranging carbon numbers. These compounds are particularly useful in chemical manufacturing, e.g., in the production of amines, amine oxides, oxo-alcohols, alkylated aromatics epoxides, tanning oils, synthetic lubricants, lubricant additives, alpha olefin sulfonates, mercaptans, organic alkyl aluminum, hydrogenated oligomers, and synthetic fatty acids. Alternatively or additionally, the ethylene may be oligomerized through LAO processes to produce C4-C20 LAOs for use as liquid blend stocks for gasoline, diesel or jet fuels. These LAOs can also be hydrogenated to linear alkanes for fuel blend stocks for gasoline, jet, and diesel fuel.

Processes used for the production of product ranges, e.g., C4-C30 LAOS, are generally referred to herein as "full range processes" or "narrow range processes", as they produce a range of chemical species, e.g., LAOs of varying chain length such as 1-butene, 1-hexene, 1-octene, 1-decene, etc., in a single process. Products from full range or narrow range processes may be distilled or fractionated into, e.g., C4-C10 LAOs for use as chemical process feedstocks, C10-C20 LAOs for use as a jet fuel blendstock, diesel fuel blendstock, and chemical feedstock. By contrast, processes that produce a single product species in high yield, e.g., LAO of a single chain length such as 1-butene, 1-hexene, 1-octene, 1-decene or the like, are referred to generally as selective processes.

Full and narrow ranges of products may be prepared from ethylene using a variety of LAO processes, such as, for example, the α-Sablin® process (See, e.g., Published International Patent Application No. WO 2009/074203, European Patent No. EP 1749806B1, and U.S. Pat. No. 8,269,055, the full disclosures of which are incorporated herein by reference in their entirety for all purposes), the Shell higher olefin process (SHOP), the Alphabutol process, the Alphahexyl process, the AlphaSelect process, the Alpha-Octol process, Linear-1 process, the Linealene process, the Ethyl Process, the Gulftene process, and the Phillips 1-hexene process.

Briefly, the α-Sablin process employs a two-component catalyst system of a zirconium salt and an aluminum alkyl co-catalyst, for homogenous, liquid phase oligomerization of ethylene to a narrow range of LAOS. The catalytic cycle comprises a chain growth step by an ethylene insertion reaction at the co-ordination site and displacement of the co-ordinated hydrocarbon from the organometallic complex. The ratio of zirconium to aluminum can be used to adjust between chain growth and displacement, thereby adjusting the product spectrum more toward lighter or heavier LAOS. For example, with a high Zr:Al ratio, the product spectrum can be shifted to upwards of 80% C4-C8 LAOS, while lower Zr:Al ratios will shift the product spectrum towards heavier LAOS. The reaction is generally carried out in a bubble column reactor with a solvent, such as toluene, and catalyst being fed into the liquid phase at temperatures of between about 60° C. and 100° C. and pressures of between about 20 bar and 30 bar. The liquid LAOs are then sent to a separation train to deactivate the catalyst, separate the solvent and optionally perform any additional product separations that are desired.

Additionally, as noted above, all or a portion of these olefinic products may be hydrogenated prior to distillation to convert the olefins into the corresponding alkanes for use as alkane blendstocks for fuel products, and then again, subjected to a distillation or other separation process to produce the desired products.

In various other embodiments, a wide range of other ethylene conversion processes may likewise be integrated at the back end of the OCM processes described above, depending upon the desired product or products for the overall process and system. For example, as noted above, in alternative or additional aspects, an integrated ethylene conversion process for production of LAOs may include the SHOP system, a full range ethylene conversion process which may be used to produce LAOs in the C6-C16 range. Briefly, the SHOP system employs a nickel-phosphine complex catalyst to oligomerize ethylene at temperatures of from about 80° C. to about 120° C., and pressures of from about 70 bar to about 140 bar.

A variety of other full-range ethylene conversion processes may be employed in the context of the invention, including without limitation, the AlphaSelect process, the Alpha-Octol process, Linear-1 process, the Linealene process, the Synthol process, the Ethyl Process, the Gulftene process, the Phillips 1-hexene process, and others. These processes are well characterized in the literature, and reported, for example at the Nexant/Chemsystems PERP report, Alpha Olefins, January 2004, the full disclosure of which are incorporated herein by reference in their entirety for all purposes.

As an alternative or in addition to full and/or narrow range ethylene conversion processes, ethylene conversion processes that may be integrated into the overall systems of the invention include processes for the selective production of high purity single compound LAO compositions. As used herein, processes that are highly selective for the production of a single chemical species are generally referred to as selective or "on purpose" processes, as they are directed at production of a single chemical species in high selectivity. In the context of LAO production, such on purpose processes will typically produce a single LAO species, e.g., 1-butene, 1-hexene, 1-octene, etc., at selectivities of greater than 50%, in some cases greater than 60%, greater than 75%, and even greater than 90% selectivity for the single LAO species.

Examples of such on purpose processes for ethylene conversion to LAOs include, for example, the Alphahexyl process from IFP, the Alphabutol process, or the Phillips 1-hexene process for the oligomerization of ethylene to high purity 1-hexene, as well as a wide range of other known processes that may be integrated with the overall OCM reactor system.

The Alphahexyl process, for example, is carried out using phenoxide ligand processes. In particular, ethylene trimerization may be carried out using a catalytic system that involves a chromium precursor, a phenoxyaluminum compound or alkaline earth phenoxide and a trialkylaluminum activator at 120° C. and 50 bar ethylene pressure (See, e.g., U.S. Pat. No. 6,031,145, and European Patent No. EP1110930, the full disclosures of which are incorporated herein by reference in their entirety for all purposes). Likewise, the Phillips 1-hexene process employs a chromium (III) alkanoate, such as chromium tris(2-ethylhexanoate, pyrrole, such as 2,5-dimethylpyrrole, and $Et_3Al$ to produce 1-hexene at high selectivity, e.g., in excess of 93%. See, e.g., European Patent No. EP0608447 and U.S. Pat. No. 5,856, 257, the full disclosures of which are incorporated herein by reference in their entirety for all purposes. A variety of other ethylene trimerization processes may be similarly integrated to the back end of the OCM systems described herein. These include, for example, the British Petroleum PNP trimerization system (see, e.g., Published International Patent Application No. WO 2002/04119, and Carter et al., Chem. Commun. 2002, 858), and Sasol PNP trimerization system (see, e.g., Published International Patent Application No. WO2004/056479, discussed in greater detail), the full disclosures of which are incorporated herein by reference in their entirety for all purposes.

The Alphabutol process employs a liquid phase proprietary soluble catalyst system of Ti(IV)/AlEt3, in the dimerization of ethylene to 1-butene at relatively high purity, and is licensed through Axens (Rueil-Malmaison, France). Ethylene is fed to a continuous liquid phase dimerization reactor. A pump-around system removes the exothermic heat of reaction from the reactor. The reactor operates between 50-60° C. at 300-400 psia. The catalyst is removed from the product effluent and is ultimately fed to the 1-butene purification column where comonomer-grade 1-butene is produced.

Still other selective ethylene conversion processes include the catalytic tetramerization of ethylene to 1-octene. For example, one exemplary tetramerization process employs a liquid phase catalytic system using a Cr(III) precursor, such as [Cr(acac)3] or $[CrCl3(THF)_3]$ in conjunction with a bis(phosphine)amine ligand and a methylaluminooxane (MAO) activator at temperatures of between about 40° C. and 80° C. and ethylene pressures of from 20 to 100 bar, to produce 1-octene with high selectivity. See, e.g., Published International Patent Application No. WO2004/056479 and Bollmann, et al., "Ethylene Tetramerization: A New Route to Produce 1-Octene in Exceptionally High Selectivities" J. Am. Chem. Soc., 2004, 126 (45), pp 14712-14713, the full disclosures of which are incorporated herein by reference in their entirety for all purposes.

In addition to the LAO processes described above, ethylene produced from the integrated OCM reactor systems can also be used to make olefinic non-LAO linear hydrocarbons and branched olefinic hydrocarbons through the same or different integrated processes and systems. For example, the ethylene product from the OCM reactor system may be passed through integrated reactor systems configured to carry out the SHOP process, the Alphabutol process, the Alphahexyl process, the AlphaSelect process, the Alpha-Octol process, Linear-1 process, the Linealene process, the Ethyl Process, the Gulftene process, and/or the Phillips 1-hexene process, to yield the resultant LAO products. The output of these systems and processes may then be subjected to an olefin isomerization step to yield linear olefins other than LAOS, branched olefinic hydrocarbons, or the like. In addition, olefinic non-LAO linear hydrocarbons and branched olefinic hydrocarbons can be prepared by ethylene oligomerization over heterogeneous catalysts such as zeolites, amorphous silica/alumina, solid phosphoric acid catalysts, as well as doped versions of the foregoing catalysts.

Other oligomerization processes have been described in the art, including the olefin oligomerization processes set forth in Published U.S. Patent Application No. 2012/0197053 (incorporated herein by reference in its entirety for all purposes), which describes processes used for production of liquid fuel components from olefinic materials.

Although a number of processes are described with certain specificity, that description is by way of example and not limitation. In particular, it is envisioned that the full range of ethylene oligomerization and/or conversion processes may be readily integrated onto the back end of the OCM reactor systems for conversion of methane to ethylene product, and subsequently to a wide range of different higher hydrocarbon products. As noted previously, certain embodiments of the ethylene conversion processes that are integrated into the overall systems of the invention are those that yield liquid hydrocarbon products. Other embodiments of the ethylene conversion processes that are integrated in the overall systems include process that are particularly well-suited for use with dilute ethylene feed stocks which optionally comprise additional components such as higher hydrocarbons, unreacted OCM starting material (methane and/or other natural gas components) and/or side products of the OCM reactions. Examples of such other components are provided above.

B. Non-Olefinic Products and Processes

In addition to or as an alternative, the ethylene product produced from the OCM reactor system may be routed through one or more catalytic or other systems and processes to make non-olefinic hydrocarbon products. For example, as noted above, saturated linear and branched hydrocarbon products may be produced from the ethylene product of the OCM reactor system through the hydrogenation of the products of the olefinic processes described above, e.g., the SHOP process, the Alphabutol process, the Alphahexyl process, the AlphaSelect process, the Alpha-Octol process, Linear-1 process, the Linealene process, the Ethyl Process, the Gulftene process, and/or the Phillips 1-hexene process.

Other catalytic ethylene conversions systems that may likewise be employed include reacting ethylene over heterogeneous catalysts, such as zeolites, amorphous silica/alumina, solid phosphoric acid catalysts, and/or doped forms of these catalysts, to produce mixtures of hydrocarbons, such as saturated linear and/or branched hydrocarbons, saturated olefinic cyclic hydrocarbons, and/or hydrocarbon aromatics. By varying the catalysts and or the process conditions, selectivity of the processes for specific components may be enhanced. For example, ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280, at ethylene partial pressures between 0.01 bar to 100 bar (undoped, or doped with Zn and/or Ga in some embodiments or some combination thereof) at temperatures above 350° C. to give high liquid hydrocarbon yield (80+%) and high aromatic selectivity (benzene, toluene, xylene (BTX) selectivity >90% within the liquid hydrocarbon fraction). Ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280, at ethylene partial pressures between 0.01 bar to 100 bar (undoped, or with dopants including but not limited to, e.g., Ni, Mg, Mn, Ca, and Co, or some combination of these) at temperatures above 200° C., to give high liquid hydrocarbon yield (80+%) and high gasoline selectivity (gasoline selectivity >90% within the liquid hydrocarbon fraction). Ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280 or a solid phosphoric acid catalyst, at ethylene partial pressures between 0.01 bar to 100 bar at temperatures above 200° C. to give high liquid hydrocarbon yield (80+%) and high distillate selectivity (gasoline selectivity >90% within the liquid hydrocarbon fraction).

In some embodiments, to achieve high jet/diesel fuel yields, a two oligomerization reactor system is used in series. The first oligomerization reactor takes the ethylene and oligomerizes it to C3-C6 olefins over modified ZSM-5 catalysts, e.g., Mg, Ca, or Sr doped ZSM-5 catalysts. The C3-C6 olefins can be the end products of the process or alternatively can be placed in a second oligomerization reactor to be coupled into jet/diesel fuel range liquid.

In addition to the foregoing processes and systems, some embodiments of the ethylene conversion processes also include processes for production of oxygenated hydrocarbons, such as alcohols and/or epoxides. For example, the ethylene product can be routed through an integrated system that includes a heterogeneous catalyst system, such as a solid phosphoric acid catalyst in the presence of water, to convert the ethylene to ethanol. This process has been routinely used to produce 200 proof ethanol in the process used by LyondellBasell. In other embodiments, longer chain olefins and/or LAO's, derived from OCM ethylene by oligomerization, can be likewise converted to alkyl alcohols using this same process. See, e.g., U.S. Pat. Nos. 2,486,980; 3,459,678; 4,012,452, the full disclosures of which are incorporated herein by reference in their entirety for all purposes. In alternate embodiments, ethylene undergoes a vapor oxidation reaction to make ethylene oxide over a silver based catalyst at 200-300° C. at 10-30 atmospheres of pressure with high selectivity (80+%). Ethylene oxide is an important precursor for synthesis of ethylene glycol, polyethylene glycol, ethylene carbonate, ethanolamines, and halohydrins. See, e.g., Chemsystems PERP Report Ethylene Oxide/Ethylene Glycol 2005.

In still other aspects, the ethylene product produced from the OCM reactor system may be routed to a reactor system that reacts the ethylene with various halogen sources (acids, gases, and others) to make halogenated hydrocarbons useful, for example, as monomers in producing halogenated polymers, such as polyvinyl chloride (PVC). For example, in one ethylene dichloride (EDC) process, available from Thyssen-Krupp Uhde, ethylene can be reacted with chlorine gas to make EDC, an important precursor to vinyl-chloride monomer (VCM) for polyvinylchloride (PVC) production. This process also can be modified EDC to react ethylene with hydrochloric acid (HCl) to make EDC via oxychlorination.

In still other exemplary ethylene conversion processes, the ethylene product of the OCM reactor system may be converted to alkylated aromatic hydrocarbons, which are also useful as chemical and fuel feedstocks. For example, in the Lummus CD-Tech EB process and the Badger EB process, benzene can be reacted with OCM ethylene, in the presence of a catalyst, to make ethylbenzene. See, e.g., U.S. Pat. No. 4,107,224, the full disclosure of which is incorporated herein by reference in its entirety for all purposes. Ethylbenzene can be added to gasoline as a high-octane gasoline blendstock or can be dehydrogenated to make styrene, the precursor to polystyrene.

In addition to the liquid and other hydrocarbons described above, in certain aspects, one or more of the integrated ethylene conversion processes is used to convert ethylene product from the OCM reactor system to one or more hydrocarbon polymers or polymer precursors. For example, in some embodiments ethylene product from the integrated OCM reactor systems is routed through an integrated Innovene process system, available through Ineos Technologies, Inc., where the ethylene is polymerized in the presence of a catalyst, in either a slurry or gas phase system, to make long hydrocarbon chains or polyethylene. By varying the process conditions and catalyst the process and system can be used to produce high density polyethylene or branched low density polyethylene, etc. The Innovene G and Innovene S processes are described at, for example, at "Ineostechnologies.com". See also Nexant/Chemsystems HDPE Report, PERP 09/10-3, January 2011, the full disclosure of which is incorporated herein by reference in its entirety for all purposes.

Alternatively, ethylene from OCM can be introduced, under high pressure, into an autoclave or tubular reactor in the presence of a free radical initiator, such as $O_2$ or peroxides, to initiate polymerization for the preparation of low-density polyethylene (LDPE). See e.g., "Advanced Polyethylene Technologies" Adv Polym Sci (2004) 169:13-27, the full disclosure of which is incorporated herein by reference in its entirety for all purposes. Alternatively, ethylene from OCM can be introduced, under low pressure in the presence of a chromium oxide based catalyst, Ziegler-Natta catalyst, or a single-site (metallocene or non metallocene based) catalyst, to prepare HDPE, MDPE, LLDPE, mLLDPE, or bimodal polyethylene. The reactor configurations for synthesis of HDPE, LLDPE, MDPE, and biomodal PE can be a slurry process, in which ethylene is polymerized to form solid polymer particles suspended in a hydrocarbon diluent, a solution process in which dissolved ethylene is polymerized to form a polymer dissolved in solvent, and/or a gas phase process in which ethylene is polymerized to form a solid polymer in a fluidized bed of polymer particles. Ethylene from OCM can be co-polymerized with different monomers to prepare random and block co-polymers. Co-monomers for ethylene copolymerization include but are not limited to: at least one olefin comonomer having three to fifteen carbons per molecule (examples are propylene and LAO's such as 1-butene, 1-hexene, 1-octene), oxygenated co-monomers such as: carbon oxide; vinyl acetate, methyl acrylate; vinyl alcohols; allyl ethers; cyclic monomers such as: norbornene and derivatives thereof; aromatic olefins such as: styrene and derivatives thereof. These ethylene or LAO copolymerization processes, e.g., where ethylene is copolymerized with different monomers, are generally referred to herein as copolymerization processes or systems.

More exemplary ethylene conversion processes that may be integrated with the OCM reactor systems include processes and systems for carrying out olefin metathesis reactions, also known as disproportionation, in the production of propylene. Olefin metathesis is a reversible reaction between ethylene and butenes in which double bonds are broken and then reformed to form propylene. "Propylene Production via Metathesis, Technology Economics Program" by Intratec, ISBN 978-0-615-61145-7, Q2 2012, the full disclosure of which is incorporated herein by reference in its entirety for all purposes. Propylene yields of about 90 wt % are achieved. This option may also be used when there is no butene feedstock. In this case, part of the ethylene from the OCM reaction feeds into an ethylene-dimerization unit that converts ethylene into butene.

As noted previously, one, two, three, four or more different ethylene conversion processes are provided integrated into the overall systems of the invention, e.g., as shown in FIG. 1. As will be appreciated, these ethylene conversion systems will include fluid communications with the OCM systems described above, and may be within the same facility or within an adjacent facility. Further, these fluid communications may be selective. In particular, in certain embodiments the interconnect between the OCM system component and the ethylene conversion system component(s) is able to selectively direct all of an ethylene product from the OCM system to any one ethylene conversion system at a given time, and then direct all of the ethylene product to a second different ethylene conversion system component at a different time. Alternatively, such selective fluid communications may also simultaneously direct portions of the ethylene product to two or more different ethylene conversion systems to which the OCM system is fluidly connected.

These fluid communications will typically comprise interconnected piping and manifolds with associated valving, pumps, thermal controls and the like, for the selective direction of the ethylene product of the OCM system to the appropriate ethylene conversion system component or components.

C. Catalysts

In certain aspects, the present invention also provides novel catalysts and catalyst compositions for ethylene conversion processes, in accordance with the above-described processes or modifications thereof. In particular, the invention provides modified zeolite catalysts and catalyst compositions for carrying out a number of desired ethylene conversion reaction processes. In particular, provided are impregnated or ion exchanged zeolite catalysts useful in conversion of ethylene to higher hydrocarbons, such as gasoline or gasoline blendstocks, diesel and/or jet fuels, as well as a variety of different aromatic compounds. For example, where one is using ethylene conversion processes to convert OCM product gases to gasoline or gasoline feedstock products or aromatic mixtures, one may employ modified ZSM catalysts, such as ZSM-5 catalysts modified with Ga, Zn, Al, or mixtures thereof. In particularly preferred aspects, Ga, Zn and/or Al modified ZSM-5 catalysts are preferred for use in converting ethylene to gasoline or gasoline feedstocks. Modified catalyst base materials other than ZSM-5 may also be employed in conjunction with the invention, including, e.g., Y, ferrierite, mordenite, and additional catalyst base materials described below.

In other aspects, ZSM catalysts, such as ZSM-5 are modified with Co, Fe, Ce or mixtures of these and are used in ethylene conversion processes using dilute ethylene streams that include both carbon monoxide and hydrogen components (See, e.g., Choudhary, et al., Microporous and Mesoporous Materials 2001, 253-267). In particular, these catalysts are capable of co-oligomerizing the ethylene and syngas components into higher hydrocarbons, and particularly mixtures useful as gasoline, diesel or jet fuel or blendstocks of these. In such embodiments, a mixed stream that includes dilute or non-dilute ethylene concentrations along with $CO/H_2$ gases is passed over the catalyst under conditions that cause the co-oligomerization of both sets of feed components. Use of ZSM catalysts for conversion of syngas to higher hydrocarbons is described in, for example, Li, et al., Energy and Fuels 2008, 22:1897-1901.

D. Reactor Systems

Reactor systems for carrying out ethylene conversion processes in accordance with the invention are also provided. A number of ethylene conversion processes employed in conjunction with the invention involve exothermic catalytic reactions where substantial heat is generated by the process. Likewise, for a number of these catalytic systems, the regeneration processes for the catalyst materials likewise involve exothermic reactions. As such, reactor systems for use in these processes will generally be configured to effectively manage excess thermal energy produced by the reactions, in order to control the reactor bed temperatures to most efficiently control the reaction, prevent deleterious reactions, and prevent catalyst or reactor damage or destruction.

As a general matter, tubular reactor configurations that present high wall surface area per unit volume of catalyst bed may generally be used for reactions where thermal control is desirable, as they permit greater thermal transfer out of the reactor. In accordance with the invention, reactor systems that include multiple parallel tubular reactors may be used in carrying out the ethylene conversion processes described herein. In particular, arrays of parallel tubular reactors each containing the appropriate catalyst for one or more ethylene conversion reaction processes may be arrayed with space between them to allow for the presence of a cooling medium between them. Such cooling medium may include any cooling medium appropriate for the given process. For example, the cooling medium may be air, water or other aqueous coolant formulations, steam, oil, or for very high temperature reactor systems, molten salt coolants. Heat exchange may additionally, or alternatively be provided to the feed gases, effluent gases, or all of them.

In one aspect, reactor systems are provided that include multiple tubular reactors segmented into one, two, three, four or more different discrete cooling zones, where each zone is segregated to contain its own, separately controlled cooling medium. The temperature of each different cooling zone may be independently regulated through its respective cooling medium and an associated temperature control system, e.g., thermally connected heat exchangers, etc. Such differential control of temperature in different reactors can be used to differentially control different catalytic reactions, or reactions that have catalysts of different age. Likewise, it allows for the real time control of reaction progress in each reactor, in order to maintain a more uniform temperature profile across all reactors, and therefore synchronize catalyst lifetimes, regeneration cycles and replacement cycles.

Figure 4:
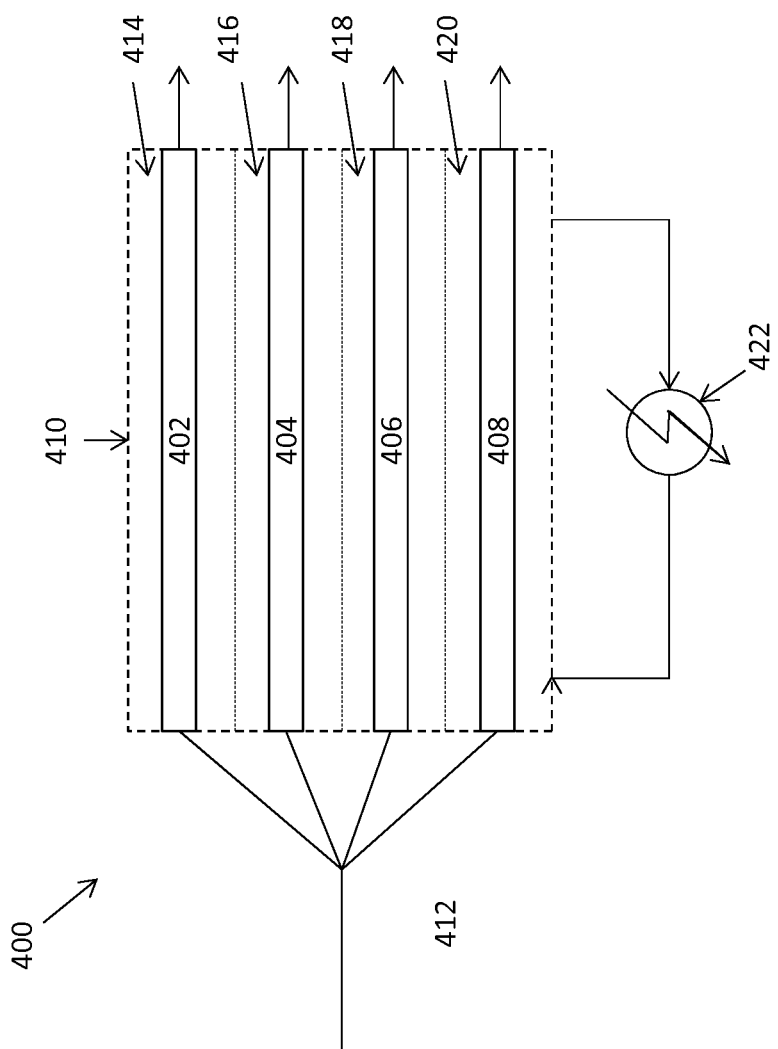
FIG. 4 schematically illustrates a tubular reactor system for use in conjunction with the present invention.

Differentially cooled tubular reactor systems are schematically illustrated in FIG. 4. As shown, an overall reactor system 400, includes multiple discrete tubular reactors 402, 404, 406, 408 contained within a larger reactor housing 410. Within each tubular reactor is disposed a catalyst bed for carrying out a desired catalytic reaction. The catalyst bed in each tubular reactor may include the same catalyst composition or it may be different from the catalyst in the other tubular reactors, e.g., optimized for catalyzing a different reaction, or for catalyzing the same reaction under different conditions. For example, in the context of the present invention, each different reactor tube may optionally include a catalyst or catalytic system for carrying out a different ethylene conversion process as described elsewhere herein.

As shown, the multiple tubular reactors 402, 404, 406, 408 share a common manifold 412 for the delivery of reactants to the reactors. However, each individual tubular reactor or subset of the tubular reactors may alternatively include a single reactant delivery conduit or manifold for delivering reactants to that tubular reactor or subset of reactors, while a separate delivery conduit or manifold is provided for delivery of the same or different reactants to the other tubular reactors or subsets of tubular reactors. Each of the different tubular reactors is separately temperature controlled, e.g., by its inclusion within a different temperature control zone which surround the reactors, e.g., zones 414, 416, 418, 420. Such control may be passive, e.g., by such zones proximity to other zones, or they may be actively controlled by being coupled to an appropriate temperature control system, e.g., such as heat exchanger 422 shown for temperature control zone 420, which may provide appropriately controlled cooling media, e.g., air, steam, molten salt, etc.

In an additional or alternative aspect, the reactor systems used in conjunction with the ethylene conversion processes described herein provide for variability in residence time for reactants within the catalytic portion of the reactor. In general, one can vary residence time within a reactor through the variation of any of a number of different applied parameters, e.g., increasing or decreasing flow rates, pressures, reactor catalyst bed lengths, etc. In accordance with certain aspects of the invention, however, a single reactor system may be provided with variable residence times, despite sharing a single reactor inlet, by varying the volume of different reactor tubes/catalyst beds or reactor tube portions within a single reactor unit. As a result of varied volumes among reactor tubes or reactor tube portions into which reactants are being introduced at a given flow rate, residence times for those reactants within those varied volume reactor tubes or reactor tube portions, will be consequently varied.

Variation of reactor volumes may be accomplished through a number of approaches. By way of example, varied volume may be provided by including two or more different reactor tubes into which reactants are introduced at a given flow rate, where the two or more reactor tubes each have different volumes, e.g., by providing varied diameters. As will be appreciated, the residence time of gases being introduced at the same flow rate into two or more different reactors having different volumes will be different. In particular, the residence time will be greater in the higher volume reactors and shorter in the smaller volume reactors. The higher volume within two different reactors may be provided by providing each reactor with different diameters. Likewise, in different embodiments y the length of the reactors catalyst bed is varied, in order to vary the volume of the catalytic portion.

Alternatively, or additionally, one can vary the volume of an individual reactor tube by varying the diameter of the reactor along its length, effectively altering the volume of different segments of the reactor. Again, in the wider reactor segments, the residence time of gas being introduced into the reactor tube will be longer in the wider reactor segments than in the narrower reactor segments.

In a related aspect, varied volumes can also be provided by routing different inlet reactant streams to different numbers of similarly sized reactor conduits or tubes. In particular, reactants, e.g., gases, may be introduced into a single reactor tube at a given flow rate to yield a particular residence time within the reactor. In contrast, reactants introduced at the same flow rate into two or more parallel reactor tubes will have a much longer residence time within those reactors.

The above-described approaches to varying residence time within reactor catalyst beds are illustrated with reference to FIGS. 5 and 6.

Figure 5:
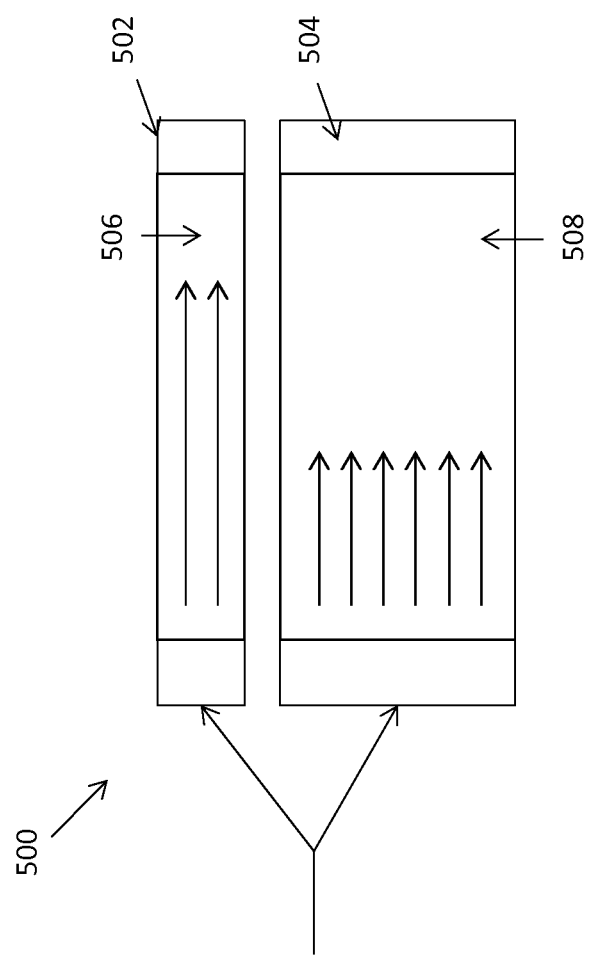
FIG. 5 schematically illustrates an exemplary reactor system that provides varied residence times for reactants.

FIG. 5 schematically illustrates a reactor system 500 in which two or more tubular reactors 502 and 504 are disposed, each having its own catalyst bed, 506 and 508, respectively, disposed therein. The two reactors are connected to the same inlet manifold such that the flow rate of reactants being introduced into each of reactors 502 and 504 are the same. Because reactor 504 has a larger volume (shown as a wider diameter), the reactants will be retained within catalyst bed 508 for a longer period. In particular, as shown, reactor 504 has a larger diameter, resulting in a slower linear velocity of reactants through the catalyst bed 508, than the reactants passing through catalyst bed 506. As noted above, one could similarly increase residence time within the catalyst bed of reactor 504 by providing a longer reactor catalyst bed. However, such longer reactor bed would be required to have similar back pressure as a shorter reactor to ensure reactants are introduced at the same flow rate as the shorter reactor.

Figure 6:
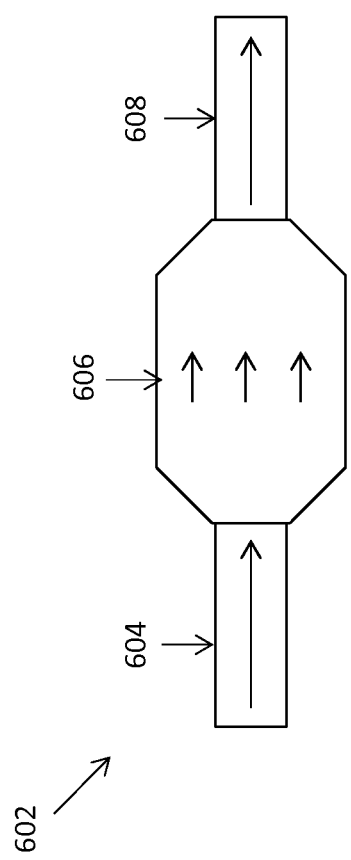
FIG. 6 schematically illustrates an alternate reactor system for varying residence times for reactants.

In FIG. 6 is schematically illustrated an alternative approach to varying reactor volumes in order to vary residence time of reactants in the catalyst bed. As shown, an individual reactor unit, e.g., reactor tube 602, is configured to provide for differing residence times within different portions of the reactor tube by varying the diameter of the reactor between reactor segment 604, 606 and 608. In particular, by providing a larger diameter of the reactor tube in segment 606 relative to segments 604 and 608, respectively, one can increase the residence time of reactants moving through these segments, as the linear velocity of the reactants through such segments decreases, as schematically illustrated by the arrows. As will be appreciated, the number and size variation of the different segments can be readily varied among reactor systems in order to achieve the desired results. In particular, a reactor may include 2, 3, 4, 5 or more different reactor segments having varied cross sectional dimensions to provide different linear flow velocities.

Again, differing residence times may be employed in catalyzing different catalytic reactions, or catalyzing the same reactions under differing conditions. In particular, one may wish to vary residence time of a given set of reactants over a single catalyst system, in order to catalyze a reaction more completely, catalyze a different or further reaction, or the like. Likewise, different reactors within the system may be provided with different catalyst systems which may benefit from differing residence times of the reactants within the catalyst bed to catalyze the same or different reactions from each other.

Alternatively or additionally, residence times of reactants within catalyst beds may be configured to optimize thermal control within the overall reactor system. In particular, residence times may be longer at a zone in the reactor system in which removal of excess thermal energy is less critical or more easily managed, e.g., because the overall reaction has not yet begun generating excessive heat. In contrast, in other zones of the reactor, e.g., where removal of excess thermal energy is more difficult due to rapid exothermic reactivity, the reactor portion may only maintain the reactants for a much shorter time, by providing a narrower reactor diameter. As will be appreciated, thermal management becomes easier due to the shorter period of time that the reactants are present and reacting to produce heat. Likewise, the reduced volume of a tubular reactor within a reactor housing also provides for a greater volume of cooling media, to more efficiently remove thermal energy.

In addition to the ethylene conversion processes described herein, components other than ethylene that are produced in an ethylene production process, e.g., contained within an OCM effluent gas, may be directed to, and thus fluidly connected to additional conversion processes in accordance with the invention. In particular, as noted above, the OCM reaction process generates a number of additional products, other than ethylene, including for example, hydrogen gas ($H_2$) and carbon monoxide (CO), also referred to as syngas. In accordance with certain aspects of the invention, the syngas component of the OCM reaction product slate is subjected to additional processing to produce other products and intermediates, e.g., dimethylether (DME), methanol, and hydrocarbons. These components may generally be useful in a variety of different end products, including liquid fuels, lubricants and propellants. In an exemplary embodiment, the syngas component of the OCM reaction effluent is separated from the other OCM products. The syngas is then subjected to any of a variety of syngas conversion processes to produce a variety of different products, e.g., methanol, dimethylether, hydrocarbons, lubricants, waxes and fuels or fuel blendstocks. In one example, the syngas component is subjected to a catalytic process to produce DME via a methanol intermediate. The catalytic process is described in detail in, e.g., U.S. Pat. No. 4,481,305, the full disclosure of which is incorporated herein by reference in its entirety for all purposes.

EXAMPLES

Example 1

Fuel Production from OCM Produced Ethylene

Figure 3:
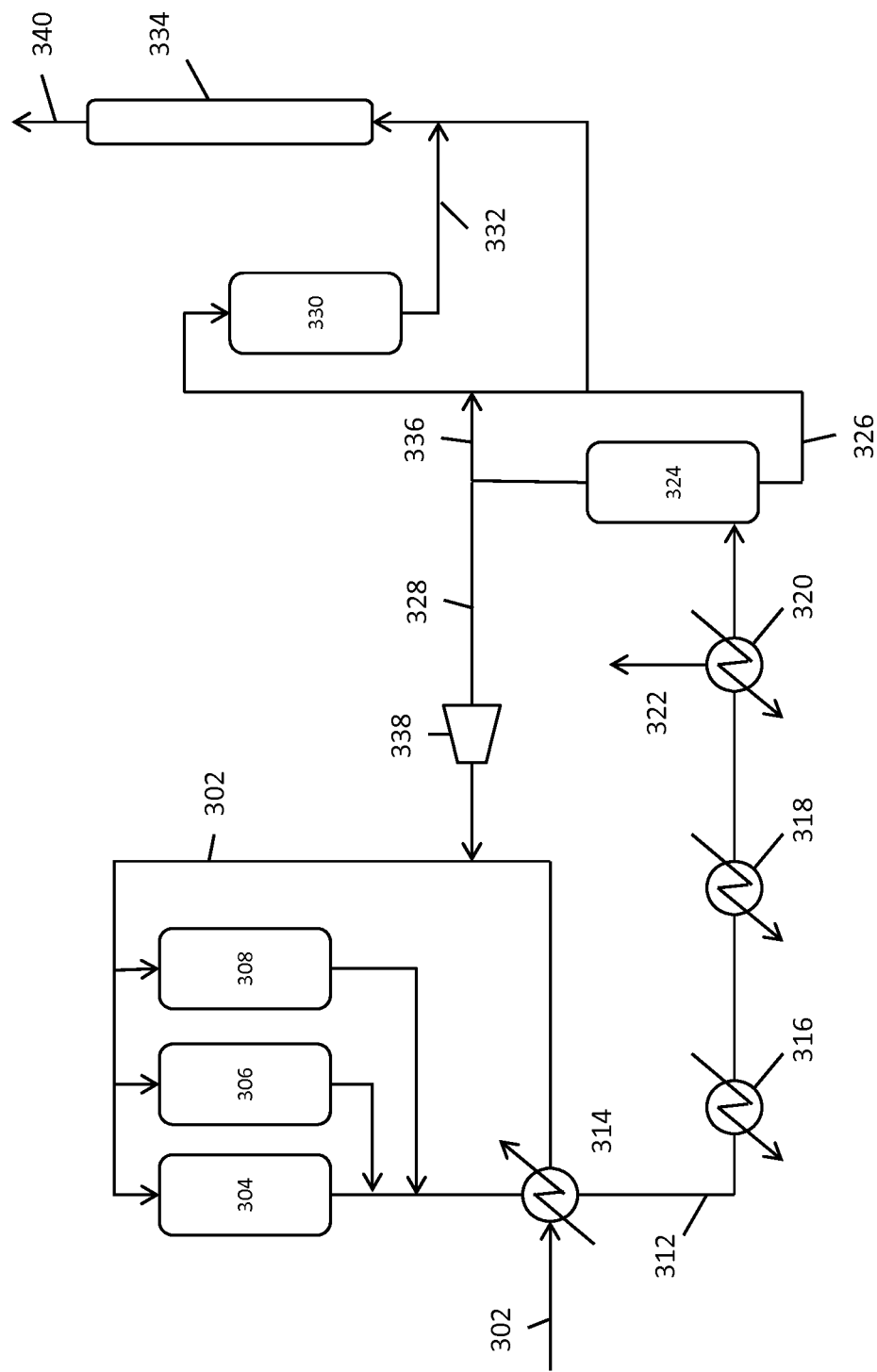
FIG. 3 schematically illustrates a process flow for conversion of ethylene to higher liquid hydrocarbons for use in, e.g., fuels and fuel blendstocks.

An exemplary liquid fuel production process is shown in FIG. 3 and described in greater detail below.

As shown in FIG. 3, an OCM product gas containing ethylene 302, is preheated to 200° to 500° C. depending upon the desired process. The ethylene may be from 0.05% to 100% pure. For less than 100% pure, the ethylene containing gas may include $CO_2$, CO, $H_2$, $H_2O$, $C_2H_6$, $CH_4$, C3 or higher hydrocarbons (i.e., C3+ hydrocarbons), or combinations thereof.

The heated ethylene containing gas 302 is then flowed through one or more ethylene conversion reactors, e.g., reactors 304, 306 and 308, each containing a solid acid catalyst. The different reactors may include reactors having the same catalyst for performing a parallel reaction to produce a single product. Alternatively, and in accordance with certain aspects of the invention, the different reactors may include different catalysts and/or be operated under different reaction conditions to produce different reaction products or product ranges. The catalysts may include crystalline catalysts, such as zeolites, e.g., zeolites ZSM-5, Y, Beta, ZSM-22, ZSM-48, SAPO-34, SAPO-5, SAPO-11, Mordenite, Ferrierite, and others. Alternatively or additionally, the catalysts may include crystalline mesoporous materials, such as SBA-15, SBA-16, MCM-22, MCM-41, and Al-MCM-41 catalysts, among others. Zeolites and mesoporous materials can be modified with metals, metal oxides, or metal ions to enhance ethylene reactivity, product slate selectivity, and/or catalyst stability.

The ethylene reacts with the solid catalyst to make higher carbon oligomers/products (C3-C30). Carbon number ranges can be targeted depending on catalyst type and process conditions.

The oligomerized ethylene product stream 312 exits from the ethylene conversion reactor(s) and may be used to heat the incoming ethylene containing gas 302, e.g., via a heat exchanger 314. The product stream is otherwise passed through a series of heat exchangers 316, 318, and 320 to cool the oligomerized product and to generate steam 322. The product stream 312 is then passed through a flash drum 324 to condense heavier products into liquids 326 and light products 336 such as C3-C4's are recycled back to the ethylene conversion reactor in stream 328 through compressor 338 for possible reaction if the C3-C4's are olefinic and/or to control the heat of reaction of the ethylene conversion reactors 304, 306 and 308. Alternatively, they may be routed through downstream processes, e.g., through hydrogenation reactor 330 in stream 336. If desired, the liquid fraction 326 is passed through a hydrogenation reactor 330 to hydrogenate olefins to paraffins/isoparaffins using a Co/Mo, Pd, Ni/Mo or other hydrogenation catalyst known in the art. The oligomerized product 326 (or optionally hydrogenated fraction 332) may then be routed to a distillation column 334 to fractionate different cuts of products 340, such as gasoline, jet, and diesel fuel, fuel blendstocks or aromatics.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. For methods recited herein, to the extent that a composition of the invention is disclosed as being provided in a method step, it will be appreciated that disclosure of such provision implicitly discloses the preparation of such composition in a transformative fashion. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure and/or application data sheet are incorporated herein by reference in their entirety for all purposes.

What is claimed is:

1. A method for producing fuel from ethylene produced by oxidative coupling of methane (OCM), the method comprising:
   (a) providing an OCM product gas comprising ethylene from an OCM process;
   (b) directing a first portion of said OCM product gas into a first ethylene conversion reactor and directing a second portion of said OCM product gas into a second ethylene conversion reactor in parallel to said first ethylene conversion reactor, said first ethylene conversion reactor and said second ethylene conversion reactor operated under different reactor conditions;
   (c) in said first ethylene conversion reactor and in said second ethylene conversion reactor, reacting said ethylene from said OCM product gas to produce first higher carbon products and second higher carbon products different from said first higher carbon products, said first higher carbon products and said second higher carbon products including $C_3$ to $C_{10}$ hydrocarbons in separate streams;
   (d) combining said separate streams into a product stream, and cooling said product stream in a heat exchanger;
   (e) directing said product stream from said heat exchanger into a flash drum that condenses said product stream to produce (i) a light product stream comprising $C_2$ to $C_4$ compounds and (ii) a heavy product stream comprising $C_4$ to $C_{10}$ compounds;
   (f) directing said light product stream to a compressor that compresses said light product stream; and
   (g) directing said light product stream from said compressor to said first ethylene conversion reactor or said second ethylene conversion reactor, thereby (i) reacting at least a portion of said $C_2$ to $C_4$ compounds from said light product stream to produce additional said first higher carbon products or second higher carbon products, or (ii) controlling a temperature in said first ethylene conversion reactor or in said second ethylene conversion reactor.

2. The method of claim 1, wherein said first higher carbon products have a first carbon number range and said second higher carbon products have a second carbon number range different than said first carbon number range.

3. The method of claim 1, further comprising fractionating said heavy product stream to produce (i) gasoline, (ii) jet fuel, (iii) diesel fuel, (iv) fuel blendstock, or (v) aromatics.

4. The method of claim 3, further comprising fractionating said heavy product stream to produce at least two of (i)-(v).

5. The method of claim 1, wherein said first ethylene conversion reactor and said second ethylene conversion reactor each comprises a zeolite catalyst.

6. The method of claim 5, wherein said zeolite catalyst includes ZSM-5.

7. The method of claim 5, wherein said first ethylene conversion reactor comprises a different zeolite catalyst than said second ethylene conversion reactor.

8. The method of claim 1, further comprising directing said heavy product stream into a hydrogenation reactor, and in said hydrogenation reactor hydrogenating said heavy product stream.

9. The method of claim 8, wherein said heavy product stream is hydrogenated with a Co/Mo, Pd, or Ni/Mo hydrogenation catalyst.

10. The method of claim 9, wherein olefins in said heavy product stream are hydrogenated to paraffins or isoparaffins in said hydrogenation reactor.

11. The method of claim 1, wherein said OCM product gas comprises between about 0.5% and about 15% ethylene.

12. The method of claim 1, wherein said OCM product gas further comprises $CO_2$, $CO$, $H_2$, $H_2O$, $C_2H_6$, $CH_4$, or $C_{3+}$ hydrocarbons, or any combination thereof.

13. The method of claim 1, wherein said OCM product gas further comprises propylene.

14. The method of claim 1, further comprising cooling said OCM product gas to a temperature between about 200° C. and 500° C. prior to (b).

15. The method of claim 14, further comprising generating steam from said cooling.

16. The method of claim 1, further comprising directing a third portion of said OCM product gas into a third ethylene conversion reactor and in said third ethylene conversion reactor, reacting said ethylene from said OCM product gas to produce higher carbon products including $C_3$ to $C_{10}$ compounds.

17. The method of claim 1, wherein each of said first higher carbon products and said second higher carbon products is generated at a selectivity greater than about 50%.

* * * * *